(12) United States Patent
Bonnert et al.

(10) Patent No.: US 7,723,373 B2
(45) Date of Patent: May 25, 2010

(54) INDOLE-3-SULPHUR DERIVATIVES

(75) Inventors: Roger Bonnert, Loughborough (GB);
Mark Dickinson, Loughborough (GB);
Rukhsana Rasul, Loughborough (GB);
Hitesh Sanganee, Loughborough (GB);
Simon Teague, Loughborough (GB)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 10/521,325

(22) PCT Filed: Jul. 15, 2003

(86) PCT No.: PCT/SE03/01216

§ 371 (c)(1),
(2), (4) Date: Aug. 15, 2005

(87) PCT Pub. No.: WO2004/007451

PCT Pub. Date: Jan. 22, 2004

(65) Prior Publication Data

US 2006/0111426 A1     May 25, 2006

(30) Foreign Application Priority Data

Jul. 17, 2002 (SE) .................... 0202241
Dec. 13, 2002 (SE) .................... 0203713

(51) Int. Cl.
*A61K 31/405* (2006.01)
*C07D 209/30* (2006.01)

(52) U.S. Cl. .................... 514/414; 514/415; 548/491
(58) Field of Classification Search .................. 548/491
See application file for complete search history.

(56) References Cited

U.S. PATENT DOCUMENTS

| | | | |
|---|---|---|---|
| 5,459,150 A | 10/1995 | Brooks et al. | |
| 5,486,525 A | 1/1996 | Summers, Jr. et al. | |
| 5,567,711 A | 10/1996 | Sheppard et al. | |
| 6,916,841 B2 | 7/2005 | Seehra et al. | |
| 6,933,316 B2 | 8/2005 | Hsieh et al. | |
| 7,166,607 B2 | 1/2007 | Bonnert et al. | |
| 2005/0222201 A1 | 10/2005 | Birkinshaw et al. | |
| 2006/0111426 A1 | 5/2006 | Bonnert et al. | |
| 2006/0264444 A1 | 11/2006 | Bonnert et al. | |
| 2008/0027092 A1 | 1/2008 | Bonnert et al. | |
| 2008/0051586 A1 | 2/2008 | Keegan et al. | |
| 2008/0249110 A1 | 10/2008 | Bonnert et al. | |
| 2009/0143449 A1 | 6/2009 | Bonnert et al. | |

FOREIGN PATENT DOCUMENTS

| EP | 0254241 | 1/1988 |
|---|---|---|
| EP | 0530907 A1 | 3/1993 |
| EP | 0576347 A1 | 12/1993 |
| EP | 0924209 B1 | 6/1999 |
| EP | 1 170 594 | 1/2002 |
| EP | 1505061 | 2/2005 |
| GB | 1 356 834 | 6/1974 |
| GB | 2422831 | 8/2006 |
| WO | WO94/19321 | 9/1994 |
| WO | WO95/16687 | 6/1995 |
| WO | WO98/13368 | 4/1998 |
| WO | WO99/09007 | 2/1999 |
| WO | WO00/78761 A1 | 12/2000 |
| WO | WO 01/32621 | 5/2001 |
| WO | WO01/47922 A2 | 7/2001 |
| WO | WO01/92224 A1 | 12/2001 |
| WO | WO03/064387 A2 | 8/2003 |
| WO | WO 03/066046 | 8/2003 |
| WO | WO 03/066047 | 8/2003 |
| WO | WO03/097598 | 11/2003 |
| WO | WO 03/101961 | 12/2003 |
| WO | WO 03/101981 | 12/2003 |
| WO | WO 2004/007451 | 1/2004 |
| WO | WO 2004/016609 A1 | 2/2004 |
| WO | WO 2004/106302 | 12/2004 |
| WO | WO 2005/019171 | 3/2005 |
| WO | WO 2005/040114 | 5/2005 |
| WO | WO 2005/054232 | 6/2005 |
| WO | WO 2006/075139 | 7/2006 |
| WO | WO 2007/138282 | 12/2007 |
| WO | WO 2007/140786 | 12/2007 |
| WO | WO 2008/000409 | 1/2008 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet; URL: http://www.cnn.com/2003/HEALTH/conditions/09/24/alzheimers.drug.ap/indexhtml>.*
Advanced Drug Delivery Reviews (2001) 48 3-26.*

(Continued)

*Primary Examiner*—Rebecca L Anderson
*Assistant Examiner*—Shawquia Young
(74) *Attorney, Agent, or Firm*—Fish & Richardson P.C.

(57) ABSTRACT

The present invention relates to substituted indoles useful as pharmaceutical compounds for treating respiratory disorders.

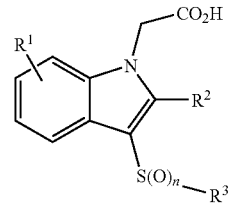

17 Claims, No Drawings

OTHER PUBLICATIONS

RN 86704-63-4, retrieved from CAPLUS search on Nov. 3, 2008.*
Ovenden et al., "Echinosulfonic Acids A-C and Echinosulfone A: Novel Bromoindole Sulfonic Acids and a Sulfone from a Southern Australian Marine Sponge, *Echinodictyum*", *J. Nat. Prod.* 62:1246-1249 (1999).
Atkinson et al., "A New Synthesis of 3-Arylthioindoles", *Synthesis* 6:480-481 (1988).
Database CA 'Online! Chemical Abstracts Service, Columbus, Ohio, US; Tanimoto, Norihiko et al: "Preparation of indole derivatives as PGD2 receptor antagonists" XP002301963 retrieved from STN Database accession No. 2003:931327.
Garcia et al., "A Novel Synthesis of 3-Cyanoindoles and a New Route to Indole-3-Carboxylic Acid Derivatives", *Tetrahedron Letters* 26(15):1827-1830 (1985).
Hamel et al., "Regioselective Synthesis of Mixed Indole 2,3-Bis-(sulfides). A Study of the Mechanism of the Second Sulfenylation of Indole", *J. Org. Chem.* 61:1573-1577 (1996).
Hary et al., "Efficient synthesis of 3-(4,5-dihydro-1*H*-imidazole-2-yl)-1*H*-indoles", *Tetrahedron Letters* 42:5187-5189 (2001).
Howard et al., "Synthesis and aldose reductase inhibitory activity of substituted 2(1*H*)-benzimidazolone- and oxindole-1-acetic acids", *Eur J Med Chem* 27:779-789 (1992).
Lüscher et al., "Deblocking of *o*-Nitrophenylsulfenyl-Protected Peptides by Ammonium Thiocyanate and (2-Methyl-1-indolyl) acetic acid", *Helv. Chim. Acta* 66(2):602-605 (1983).
Matassa et al., "Evolution of a Series of Peptidoleukotriene Antagonists: Synthesis and Structure/ Activity Relationships of 1,3,5-Substituted Indoles and Indazoles", *J. Med. Chem.* 33:1781-1790 (1990).
Matsugi et al., "An efficient sylfenylation of aromatics using highly active quinone mono *O,S*-acetal bearing a pentafluorophenylthio group", *Tetrahedron Letters* 42:1077-1080 (2001).
Matsugi et al., "Facile and Efficient Sulfenylation Method Using Quinone Mono-*O,S*-Acetals under Mild Conditions", *J. Org. Chem.* 66:2434-2441 (2001).
STN International, CAPLUS accession No. 1977:535057, Document No. 87:135057, Sankyo Co., Ltd., "3-Indolyl thio ethers", & JP,A2,52039671, 19770328, RN 64137-76-4, 54491-43-9, 56366-45-1.
STN International, CAPLUS accession No. 1980:6356, Document No. 92:6356, Gabrielyan, G.E. et al.: "Indole derivatives. LX. Synthesis of indole compounds with a furan ring", & Armyanskii Khimicheskii Zhurnal (1979), 32(4), 309-14, RN 51842-57-0.
STN International, CAPLUS accession No. 2001:235566, Document No. 134:266203, Kato, Susumu et al.: "Preparation and application of benzopyranone derivatives"; & JP,A2,2001089471, 20010403, RN 332082-10-7.
STN International, CAPLUS accession No. 2001:338492, Document No. 134:353315, Wakunaga Pharmaceutical Co., Ltd., "Preparation of indole derivatives as chymase inhibitors and drugs containing the same as the active ingredient", & WO,A1,2001032621, 20010510, RN 64137-76-4, 336186-33-5.
STN International, CHEMCATS accession No. 2000:1027702, Apr. 26, 2001, 8004-3013, "1H-Indole-1-acetic acid, 2-methyl-3-(phenylthio)-, ethyl ester", CAS Registry No. 300860-50-8.
STN International, file CAPLUS, CAPUS accession No. 1995:401159, Document No. 122:187576, Yoshitomi Pharmaceutical Industries, Ltd., "Preparation of fused pyrazole derivatives", & JP,A2, 06206872, 19940726.
Morissette et al., "High-throughput crystallization: polymorphs, salts, co-crystals and solvates of pharmaceutical solids", *Advanced Drug Delivery Reviews* 56:275-300 (2004).
Patani and LaVoie, "Bioisosterism: A Rational Approach in Drug Design", *Chem Rev.* 96:3147-3176 (1996).
"COPD: Causes and Prevention." NIH SeniorHealth. National Heart, Lung, and Blood Institute. Accessed Apr. 6, 2009. <http://nihseniorhealth.gov/copd/causesandprevention/01.html>.
"Prevention of Cystic Fibrosis." WrongDiagnosis.com. Accessed Apr. 6, 2009. <http://www.wrongdiagnosis.com/c/cf/prevent.htm>.

* cited by examiner

INDOLE-3-SULPHUR DERIVATIVES

CROSS-REFERENCE TO RELATED APPLICATIONS

This application is the national phase application under 35 U.S.C. §371 of PCT International Application No. PCT/SE2003/001216, filed Jul. 15, 2003, which claims priority to Swedish Application Serial No. 0202241-6, filed Jul. 17, 2002, and Swedish Application Serial No. 0203713-3, filed Dec. 13, 2002.

The present invention relates to substituted indoles useful as pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTh2. GB 1356834 discloses a series of compounds said to possess anti-inflammatory, analgesic and antipyretic activity. It has now surprisingly been found that certain indole acetic acids are active at the CRTh2 receptor, and as a consequence are expected to be potentially useful for the treatment of various respiratory diseases, including asthma and COPD.

In a first aspect the invention therefore provides a compound of formula (I) or a pharmaceutically acceptable salt thereof:

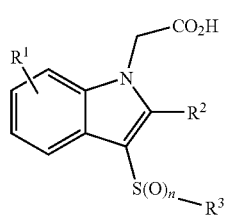

(I)

in which:

n represents 1 or 2;

$R^1$ is one or more substituents independently selected from halogen, CN, nitro, $SO_2R^4$, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, aryl, heteroaryl, $C_2$-$C_6$ alkenyl, $C_2$-$C_6$ alkynyl or $C_{1-6}$alkyl, the latter five groups being optionally substituted by one or more substituents independently selected from halogen, $OR^7$ and $NR^8R^9$, $NR^8R^9$, $S(O)_xR^7$ where x is 0, 1 or 2;

$R^2$ is hydrogen, halogen, CN, $SO_2R^4$ or $CONR^5R^6$, $COR^4$ or $C_{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is aryl or a 5-7 membered heteroaryl ring containing one or more heteroatoms selected from N, S and O, each of which is optionally substituted by one or more substituents independently selected from halogen, CN, nitro, $SO_2R^4$, OH, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, $C_2$-$C_6$ alkenyl, $C_2$-$C_6$ alkynyl, $C_1$-$C_6$ alkyl, the latter three groups being optionally substituted by one or more substituents independently selected from halogen atoms, $OR^7$ and $NR^8R^9$, $S(O)_xR^7$ where x is 0, 1 or 2;

$R^4$ represents aryl, heteroaryl, or $C_1$-$C_6$ alkyl, all of which may be optionally substituted by one or more substituents independently selected from halogen atoms, aryl, heteroaryl, $OR^{10}$ and $NR^{11}R^{12}$ $S(O)_xR^{13}$ (where x=0, 1 or 2), $CONR^{14}R^5$, $NR^{14}COR^{15}$, $SO_2NR^{14}R^{15}$, $NR^{14}SO_2R^{15}$, CN, nitro;

$R^5$ and $R^6$ independently represent a hydrogen atom, a $C_1$-$C_6$ alkyl group, an aryl, or a heteroaryl, the latter three of which may be optionally substituted by one or more substituents independently selected from halogen atoms, aryl, $OR^{13}$ and $NR^{14}R^{15}$, $CONR^{14}R^{15}$, $NR^{14}COR^{15}$, $SO_2NR^{14}R^{15}$, $NR^{14}SO_2R^{15}$, CN, nitro; or $R^5$ and $R^6$ together with the nitrogen atom to which they are attached can form a 3-8 membered saturated heterocylic ring optionally containing one or more atoms selected from O, S(O), where x is 0, 1 or 2, $NR^{16}$, and the ring itself optionally substituted by $C_1$-$C_3$ alkyl;

$R^7$ and $R^{13}$ independently represent a $C_1$-$C_6$ alkyl group, an aryl or heteroaryl group all of which may be optionally substituted by halogen atoms;

$R^8$ represents a hydrogen atom, $C(O)R^9$, $C_1$-$C_6$ alkyl (optionally substituted by halogen atoms, aryl or heteraryl groups, both of which may also be optionally substituted by one or more fluorine atoms); an aryl or a heteroaryl group, which may be optionally substituted by one or more halogen atoms;

each of $R^9$, $R^{10}$, $R^{11}$, $R^{12}$, $R^{14}$, $R^{15}$, independently represents a hydrogen atom, $C_1$-$C_6$ alkyl, an aryl or a heteroaryl group (all of which may be optionally substituted by one or more halogen atoms); and $R^{16}$ is hydrogen, $C_{1-4}$ alkyl, —$C(O)C_1$-$C_4$ alkyl, $C(O)YC_1$-$C_4$alkyl, Y is O or $NR^7$.

In the context of the present specification, unless otherwise indicated, an alkyl or alkenyl group or an alkyl or alkenyl moiety in a substituent group may be linear, branched or cyclic.

Aryl is phenyl and naphthyl.

When $R^3$ is heteroaryl, examples include pyridine, pyrimidine, thiazole, oxazole, pyrazole, imidazole, furan, isoxazole, pyrrole, isothiazole and azulene.

When $R^4$ is heteroaryl this includes 5-6 membered aromatic ring or can be a 6,6- or 6,5-fused bicyclic ring system, each ring containing one or more heteroatoms selected from N, S and O. Examples include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8,-naphthyridine, pteridine, quinolone.

Heterocyclic rings as defined for $R^5$ and $R^6$ means saturated heterocycles, examples include morpholine, thiomorpholine, azetidine, imidazolidine, pyrrolidine, piperidine and piperazine.

Preferably n is 2.

Preferably $R^1$ is halogen, nitrile, $C_{1-6}$alkyl or $SO_2R^4$, $NO_2$, $NR^9COR^4$, $NR^9SO_2R^4$, aryl, $NR^5R^6$. More preferably $R^1$ is methyl, nitrile, chloro, $SO_2Me$, $SO_2Et$, $NHCOR^4$, $NHSO_2R^4$, phenyl, NH(alkyl).

The $R^1$ group(s) can be present at any suitable position on the indole ring, preferably the $R^1$ group(s) is (are) at the 5-position and/or 4-position. Preferably the number of substituents $R^1$ other than hydrogen is 1 or 2.

Preferably $R^2$ is $C_{1-6}$alkyl, more preferably methyl.

Preferably $R^3$ is phenyl optionally substituted by halogen, $C_1$-$C_6$ alkyl, $C_1$-$C_6$alkloxy or nitrile. More preferably $R^3$ is phenyl optionally substituted by chloro, methyl, ethyl, cyano or methoxy.

Substituents can be present on any suitable position of an R³ group.

Preferred compounds of the invention include:
3-[(4-chlorophenyl)sulfonyl]-2,5-dimethyl-1H-indol-1-acetic acid;
5-chloro-3-[(4-chlorophenyl)sulfonyl]-2-methyl-1H-indole-1-acetic acid;
6-chloro-3-[(4-chlorophenyl)sulfonyl]-2-methyl-1H-indole-1-acetic acid;
7-chloro-3-[(4-chlorophenyl)sulfonyl]-2-methyl-1H-indole-1-acetic acid;
5-chloro-3-[(4-chlorophenyl)sulfonyl]4-cyano-2-methyl-1H-indole-1-acetic acid;
5-chloro-3-[(4-chlorophenyl)sulfonyl]-6-cyano-2-methyl-1H-indole-1-acetic acid;
3-[(4-chlorophenyl)sulfinyl]-2,5-dimethyl-1H-indole-1-acetic acid;
3-[(4-chlorophenyl)sulfonyl]-4-(ethylsulfonyl)-7-methoxy-2-methyl-1H-indole-1-acetic acid;
3-[(4-chlorophenyl)sulfinyl]-5-cyano-2-methyl-1H-indole-1-acetic acid;
3-[(4-chlorophenyl)sulfonyl]-5-cyano-2-methyl-1H-indole-1-acetic acid;
5-chloro-3-[(4-chlorophenyl)sulfonyl]-2-methyl-1H-indole-1-acetic acid, sodium salt;
4-chloro-3-[(4-chlorophenyl)sulfonyl]-2-methyl-1H-indole-1-acetic acid;
3-[(4-methoxyphenyl)sulfonyl]-2,5-dimethyl 1H-indol-1-acetic acid;
3-[(3-methoxyphenyl)sulfonyl]-2,5-dimethyl-1H-indol-1-acetic acid;
3-[(2-chlorophenyl)sulfonyl]-2,5-dimethyl-1H-indol-1-acetic acid;
3-[(3-chlorophenyl)sulfonyl]-2,5-dimethyl-1H-indol-1-acetic acid;
3-[(4-cyanophenyl)sulfonyl]-2,5-dimethyl-1H-indole-1-acetic acid;
3-[(2-methylphenyl)sulfonyl]-2,5-Dimethyl-1H-indol-1-acetic acid;
3-[(2-ethylphenyl)sulfonyl]-2,5-dimethyl-1H-indol-1-acetic acid;
3-[(4-chlorophenyl)sulfonyl]-2-methyl-4-nitro-1H-indole-1-acetic acid;
4-(acetylamino)-3-[(4-chlorophenyl)sulfonyl]-2-methyl-1H-indole-1-acetic acid;
3-[(4-chlorophenyl)sulfonyl]-2-methyl-4-[(methylsulfonyl)amino]-1H-indole-1-acetic acid;
3-[(4-chlorophenyl)sulfonyl]-4-(ethylamino)-2-methyl-1H-indole-1-acetic acid;
3-[(2,6-Dichlorophenyl)sulfonyl]-2,5-dimethyl-1H-indole-1-acetic acid;
3-[(4-chlorophenyl)sulfonyl]-2-methyl-4-phenyl-1H-indole-1-acetic acid
3-[(4-chlorophenyl)sulfonyl]-5-fluoro-2-methyl-1H-indole-1-acetic acid,
3-[(3-chlorophenyl)sulfonyl]-5-fluoro-2-methyl-1H-indole-1-acetic acid,
5-fluoro-2-methyl-3-[[4-(trifluoromethyl)phenyl]sulfonyl]-1H-indole-1-acetic acid, and pharmaceutically acceptable salts thereof.

In a further aspect the invention provides a sub-class of compounds of formula (IA):

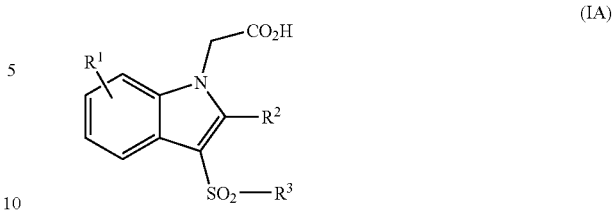

(IA)

in which
$R^1$ and $R^2$ are independently hydrogen, halogen, CN, amino, nitro, $C_{1-6}$alkyl, $C_{1-6}$alkoxy, $SO_2C_{1-6}$alkyl or $CONR^4R^5$ where $R^4$ and $R^5$ independently hydrogen or $C_{1-6}$alkyl; and
$R^3$ is phenyl substituted by halogen, and pharmaceutically acceptable salts thereof.

Preferably for compounds (IA) $R^1$ is hydrogen or $C_{1-6}$alkyl. More preferably $R^1$ is methyl. The $R^1$ group can be present at any suitable position on the indole ring, preferably the $R^1$ group is at the 5-position.

Preferably for compounds (IA) $R^2$ is $C_{1-6}$alkyl, more preferably methyl.

Preferably for compounds (IA) $R^3$ is phenyl substituted by chloro.

Preferred compounds (IA) include:
{3-[(4-chlorophenyl)sulfonyl]-2,5-dimethyl-1H-indol-1-yl}acetic acid.

and pharmaceutically acceptable salts thereof.

In a further aspect the inevtion provides a further sub-class of compounds of formula (IB):

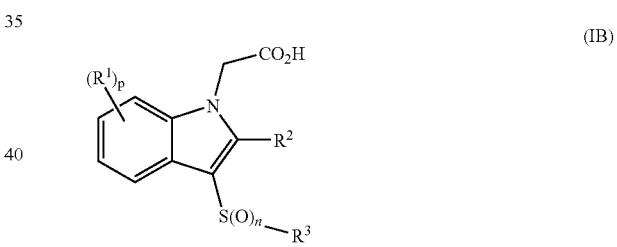

(IB)

in which:
n represents 1 or 2;
$R^1$ is halogen, CN, nitro, $SO_2R^4$, $OR^4$, $SR^4$, $SO_2R^4$, $SO_2NR^5R^6$, $CONR^5R^6$, $NR^5R^6$, $NR^7SO_2R^4$, $NR^7CO_2R^4$, $C_2-C_6$ alkenyl, $C_2-C_6$ alkynyl or $C_{1-6}$alkyl, the latter three groups being optionally substituted by one or more substituents independently selected from halogen, —$OR^7$ and —$NR^8R^9$, $S(O)_xR^7$ where x is 0, 1 or 2;
p is 0 to 4;
$R^2$ is hydrogen, halogen, CN, $SO_2R^4$ or $CONR^5R^6$, $COR^4$ or $C_{1-7}$alkyl, the latter three groups being optionally substituted by one or more substituents independently selected from halogen atoms, —$OR^7$ and —$NR^8R^9$, $S(O)_xR^7$ where x is 0, 1 or 2:
$R^3$ is $R^3$ is phenyl optionally substituted by halogen;
$R^4$ represents hydrogen or $C_{1-6}$alkyl which may be optionally substituted by one or more substituents independently selected from halogen atoms, aryl, —$OR^{10}$ and —$NR^{11}R^{12}$.
$R^5$ and $R^6$ independently represent a hydrogen atom, a $C_{1-6}$alkyl group, or phenyl group the latter two of which may be optionally substituted by one or more substituent groups independently selected from halogen atoms, aryl, —$OR^{13}$ and —$NR^{14}R^{15}$, —$CONR^{14}R^{15}$, —$NR^{14}COR^{15}$, —$SO_2NR^{14}R^{15}$, $NR^{14}SO_2R^{15}$;

or $R^5$ and $R^6$ together with the nitrogen atom to which they are attached can form a 3-8 membered saturated heterocylic ring optionally containing one or more atoms selected from O, S, $NR^{16}$, and itself optionally substituted by $C_{1-3}$ alkyl, halogen;

each of $R^7$, $R^8$, $R^9$ $R^{10}$, $R^{11}$, $R^{12}$, $R^{13}$, $R^{14}$, $R^{15}$, independently represents a hydrogen atom, $C_1$-$C_6$, alkyl, or an aryl group; and $R^{16}$ is hydrogen, $C_{1-4}$ allyl, —$COC_1$-$C_4$ alkyl, —$COYC_1$-$C_4$alkyl, Y=O or $NR^7$.

Preferably for compounds (IB) $R^1$ is halogen, nitrile, $C_{1-6}$alkyl or $SO_2R^4$. More preferably $R^1$ is methyl, nitrile, chloro, $SO_2Me$, $SO_2Et$ Preferably p is 1 or 2.

The $R^1$ groups can be present at any suitable position on the indole ring. preferably the $R^1$ group(s) is (are) at the 5-position and/or 4-position.

Preferably for compounds (IB) $R^2$ is $C_{1-6}$alkyl, more preferably methyl.

Preferably for compounds (IB) $R^3$ is phenyl optionally substituted by halogen, more preferably chloro.

Preferred compounds (BB) include:
{3-[(4-chlorophenyl)sulfonyl]-2,5-dimethyl-1H-indol-1-yl}acetic acid,
5-chloro-3-[(4-chlorophenyl)sulfonyl]-2-methyl-1H-indole-1-acetic acid,
6-chloro-3-[(4-chlorophenyl)sulfonyl]-2-methyl-1H-indole-1-acetic acid,
7-chloro-3-[(4-chlorophenyl)sulfonyl]-2-methyl-1H-indole-1-acetic acid,
5-chloro-3-[(4-chlorophenyl)sulfonyl]4-cyano-2-methyl-1H-indole-1-acetic acid,
5-chloro-3-[(4-chlorophenyl)sulfonyl]-6-cyano-2-methyl-1H-indole-1-acetic acid,
3-[(4-chlorophenyl)sulfinyl]-2,5-dimethyl-1H-indole-1-acetic acid,
3-[(4-chlorophenyl)sulfonyl]-4-(ethylsulfonyl)-7-methoxy-2-methyl-1H-indole-1-acetic acid,
3-[(4-chlorophenyl)sulfinyl]-5-cyano-2-methyl-1H-indole-1-acetic acid,
3-[(4-chlorophenyl)sulfonyl]-5-cyano-2-methyl-1H-indole-1-acetic acid,
Sodium 5-chloro-3-[(4-chlorophenyl)sulfonyl]-2-methyl-1H-indole-1-acetate, and pharmaceutically acceptable salts thereof.

In a still further aspect the invention provides the use of a compound of formula (IC) or a pharmaceutically acceptable salt thereof in the manufacture of a medicament for the treatment of a disease where the inhibition of CRTh2 is beneficial:

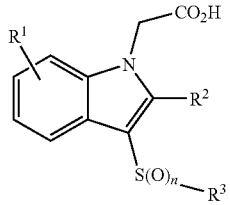

(IC)

in which:
n represents 1 or 2;
$R^1$ is one or more substituents independently selected from halogen, CN, nitro, $SO_2R^4$, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, aryl, heteroaryl, $C_2$-$C_6$ alkenyl, $C_2$-$C_6$ alkynyl or $C_{1-6}$alkyl, the latter five groups being optionally substituted by one or more substituents independently selected from halogen, $OR^7$ and $NR^8R^9$, $NR^8R^9$, $S(O)_xR^7$ where x is 0, 1 or 2;

$R^2$ is hydrogen, halogen, CN, $SO_2R^4$ or $CONR^5R^6$, $COR^4$ or $C_{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is aryl or a 5-6 membered or 6,6- or 6,5-fused bicyclic aromatic ring each containing one or more heteroatoms selected from N, S and O, and each of which is optionally substituted by one or more substituents independently selected from halogen, CN, nitro, $SO_2R^4$, OH, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, $C_2$-$C_6$ alkenyl, $C_2$-$C_6$ alkynyl, $C_1$-$C_6$ alkyl, the latter three groups being optionally substituted by one or more substituents independently selected from halogen atoms, $OR^7$ and $NR^8R^9$, $S(O)_xR^7$ where x is 0, 1 or 2;

$R^4$ represents aryl, heteroaryl, or $C_1$-$C_6$ alkyl, all of which may be optionally substituted by one or more substituents independently selected from halogen atoms, aryl, heteroaryl, $OR^{10}$ and $NR^{11}R^{12}$ $S(O)_xR^{13}$ (where x=0, 1 or 2), $CONR^{14}R^{15}$, $NR^{14}COR^{15}$, $SO_2NR^{14}R^{15}$, $NR^{14}SO_2R^{15}$, CN, nitro;

$R^5$ and $R^6$ independently represent a hydrogen atom, a $C_1$-$C_6$ alkyl group, an aryl, or a heteroaryl, the latter three of which may be optionally substituted by one or more substituents independently selected from halogen atoms, aryl, $OR^{13}$ and $NR^{14}R^{15}$, $CONR^{14}R^{15}$, $NR^{14}COR^{15}$, $SO_2NR^{14}R^{15}$, $NR^{14}SO_2R^{15}$, CN, nitro;

or $R^5$ and $R^6$ together with the nitrogen atom to which they are attached can form a 3-8 membered saturated heterocylic ring optionally containing one or more atoms selected from O, $S(O)_x$ where x is 0, 1 or 2, $NR^{16}$, and the ring itself optionally substituted by $C_1$-$C_3$ alkyl;

$R^7$ and $R^{13}$ independently represent a $C_1$-$C_6$ alkyl group, an aryl or heteroaryl group all of which may be optionally substituted by halogen atoms;

$R^8$ represents a hydrogen atom, $C(O)R^9$, $C_1$-$C_6$ alkyl (optionally substituted by halogen atoms, aryl or heteraryl groups, both of which may also be optionally substituted by one or more fluorine atoms); an aryl or a heteroaryl group, which may be optionally substituted by one or more halogen atoms;

each of $R^9$, $R^{10}$, $R^{11}$, $R^{12}$, $R^{14}$, $R^{15}$, independently represents a hydrogen atom, $C_1$-$C_6$ alkyl, an aryl or a heteroaryl group (all of which may be optionally substituted by one or more halogen atoms); and $R^{16}$ is hydrogen, $C_{1-4}$ alkyl, —$C(O)C_1$-$C_4$ alkyl, $C(O)YC_1$-$C_4$alkyl, Y is O or $NR^7$.

As used below, the term "compound of formula (I)" refers to any compound above of formula (I), (IA), (IB) or (IC).

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate. Preferred salts include sodium salts.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (I) can be prepared by:
(a) oxidation of a compound of formula (II):

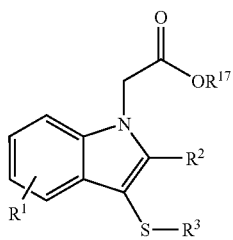
(II)

in which $R^{17}$ is hydrogen or alkyl and $R^1$, $R^2$ and $R^3$ are as defined in formula (I) or are protected derivatives thereof, or
(b) reaction of a compound of formula (III):

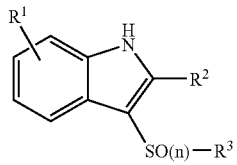
(III)

in which $R^1$, $R^2$ and $R^3$ are as defined in formula (I) or are protected derivatives thereof, with a compound of formula (I):

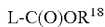 L-C(O)OR$^{18}$  (IV)

where $R^{18}$ is an alkyl group and L is a leaving group in the presence of a base, and optionally thereafter (a) or (b) in any order:
  hydrolysing the ester group $R^{17}$ or $R^{18}$ to the corresponding acid
  removing any protecting group
  forming a pharmaceutically acceptable salt.

For process (a) suitable oxidising agents include MCPBA, $H_2O_2$ or oxone. When $R^{17}$ is alkyl, ethyl, methyl or tertiary-butyl groups are preferred. Where $R^{17}$ is hydrogen compounds of formula (I) are obtained directly by optionally removing of a protecting group and formation of appropriate salts.

Where $R^{17}$ is alkyl the corresponding ester can be hydrolysed. Hydrolysis of the ester group $R^{17}$ can be carried out using routine procedures, for example by stirring with base, preferably aqueous sodium or lithium hydroxide, or stirring with an acid such as TFA and optionally removing of protecting groups and formation of appropriate salts.

For process (b) the reaction can be carried out in a suitable solvent such as THF using a base such as sodium hydride or the like. Suitable groups $R^{18}$ include C1ot alkyl groups such as methyl, ethyl or tertiary-butyl. Suitable L is a leaving group such as halo, in particular bromo. Preferably the compound of formula (IV) is ethyl bromoacetate.

Hydrolysis of the ester group $R^{18}$ can be carried out using routine procedures as described above for $R^{17}$.

Compounds of formula (III) can be prepared by reaction of a compound of formula (V) using process (a):

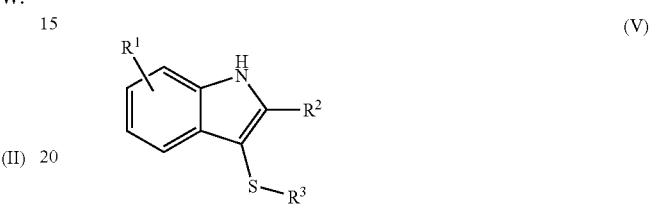
(V)

in which $R^1$, $R^2$ and $R^3$ are as defined in formula (I) or are protected derivatives thereof, with an oxidising agent, and optionally thereafter removing any protecting group.

Compounds of formula (V) where $R^1$, $R^2$ and $R^3$ are as defined in formula (I) or are protected derivatives thereof can be prepared by reacting a compound of formula (VI) with a compound of formula (VII):

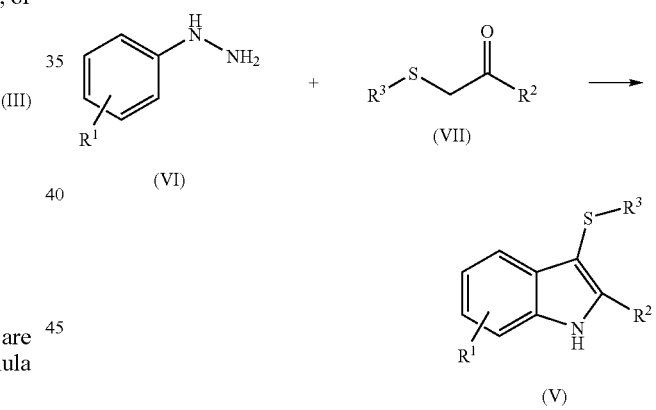

in which $R^1$, $R^2$ and $R^3$ are as defined in formula (I), or protected derivatives thereof.

Preferably the reaction is carried out in acetic acid with heating.

Or, compounds of formula (V) where $R^1$, $R^2$ and $R^3$ are as defined in formula (I) or are protected derivatives thereof, can be prepared by reacting a compound of formula (VIII) with a compound of formula (VII):

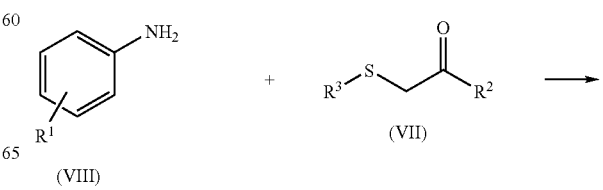

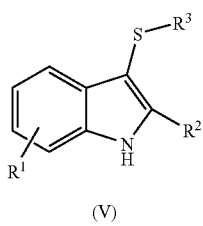

(V)

Compounds of formula (VI), (VII) and (VIII) are commercially available or can be prepared using standard chemistry well known in the art. Where $R^1$, $R^2$ and $R^3$ are as defined in formula (I) or are protected derivatives thereof. Preferably the reaction is carried out in a suitable solvent, such as dichloromethane or THF in the presence of a chlorinating agent such as sulfonyl cloride or tertiary-butyl hypochlorite.

Alternatively compounds of formula (I) can be prepared by reacting compounds of formula (IX) with compounds of formula (X). Where $R^1$, $R^2$ and $R^3$ are as defined in formula (I) or are protected derivatives thereof.

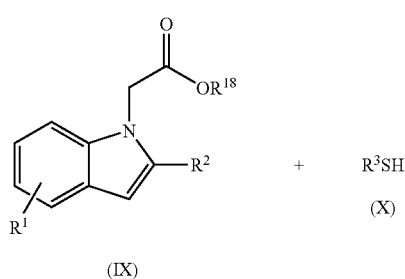

(IX)

(X)

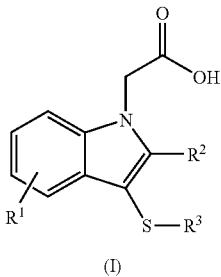

(I)

Preferably the reaction is carried out in a suitable solvent such as ethanol or DMF, in the presence of iodine.

Compounds of formula (IX) can be prepared by reaction of compounds of formula (XI) and (IV) as outlined above.

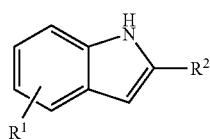

(XI)

Compounds of formula (X) and (XI) are commercially available or can be prepared using standard chemistry well known in the art. Where $R^1$, $R^2$ and $R^3$ are as defined in formula (I) or are protected derivatives thereof.

Compounds of formula (II) in which $R^1$ is aryl are prepared from compounds of formula (II) in which $R^1$ is halogen, preferably bromine or iodine using Suzuki coupling conditions, preferably using tetrakistriphenylphosphine palladium (0) as a catalyst in a suitable organic solvent, such as toluene, with heating.

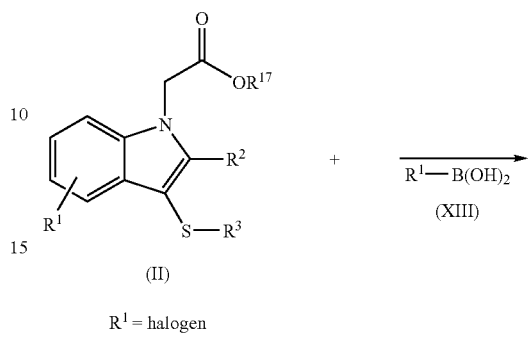

(II)

$R^1$ = halogen

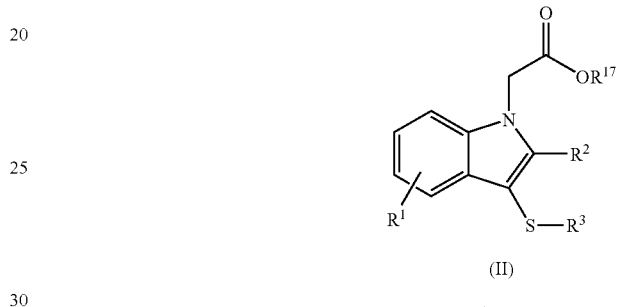

(II)

$R^1$ = aryl

Compounds of formula (II) in which $R^1$ is $NR^9SO_2R^4$ are prepared from compounds of formula (XII) by reacting with a suitable base, preferably sodium hydroxide.

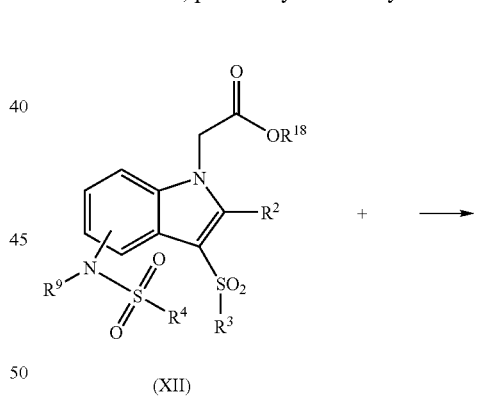

(XII)

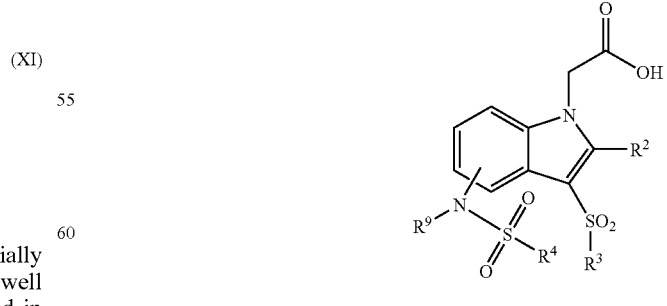

(I)

Compounds of formula (XII) are prepared from compounds of formula (XIII)

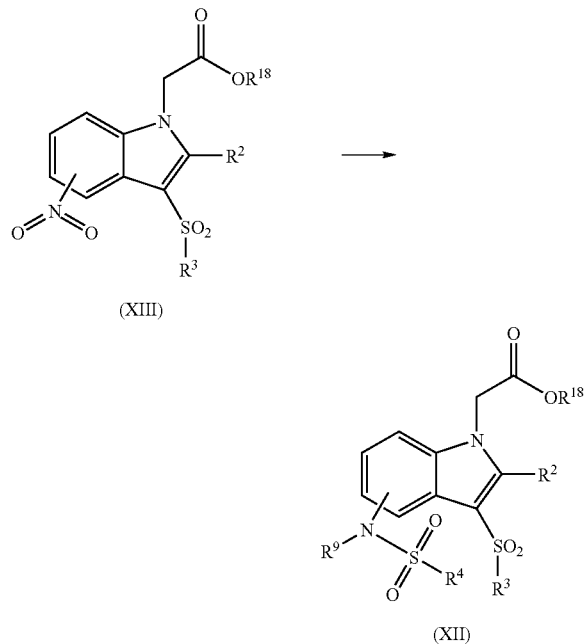

Compounds of formula (XIII) are hydrogenated in the presence of a suitable catalyst such as platinum on charcoal, in acidic conditions. The product of this reaction is then reacted with a sulfonyl chloride compound in the presence of a base, preferably triethylamine in an organic solvent, such as acetonitrile.

Compounds of formula (XIII) are prepared from compounds of formula (II) in which $R^1$ is $NO_2$, by reaction with a suitable oxidising agent (process A).

Compounds of formula (I) in which $R^1$ is NRCOR are prepared by hydrogenation of a compound of formula (II) in which $R^1$ is nitro, as outlined for compounds of formula (XII) above. The reduced product is then treated with an acyl chloride [ClC(O)$R^4$] in the presence of base to give a compound of formula (II), this is subsequently hydrolysed and oxidised (processes a and b) to give a compound of formula (I) as outlined previously.

The compounds of formula (I) have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites. Examples of such conditions/diseases include:

(1) (the respiratory tract) obstructive airways diseases including: asthma (such as bronchial, allergic, intrinsic, extrinsic and dust asthma particularly chronic or inveterate asthma (e.g. late asthma and airways hyper-responsiveness)); to chronic obstructive pulmonary disease (COPD)(such as irreversible COPD); bronchitis (including eosinophilic bronchitis); acute, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofoulous rhinitis, perennial allergic rhinitis, easonal rhinitis (including rhinitis nervosa (hay fever) and vasomotor rhinitis); nasal polyposis; sarcoidosis; farmer's lung and related diseases; fibroid lung; idiopathic interstitial pneumonia; cystic fibrosis; antitussive activity, treatment of chronic cough associated with inflammation or iatrogenic induced;

(2) (bone and joints) arthrides including rheumatic, infectious, autoimmune, seronegative, spondyloarthropathies (such as ankylosing spondylitis, psoriatic arthritis and Reiter's disease), Behcet's disease, Sjogren's syndrome and systemic sclerosis;

(3) (skin and eyes) psoriasis, atopical dermatitis, contact dermatitis, other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, chronic skin ulcers, uveitis, Alopecia greatacorneal ulcer and vernal conjunctivitis;

(4) (gastrointestinal tract) Coeliac disease, proctitis, eosinopilic gastro-enteritis, mastocytosis, Crohn's disease, ulcerative colitis, irritable bowel disease; food-related allergies which have effects remote from the gut, (such as migraine, rhinitis and eczema);

(5) (central and peripheral nervous system) Neurodegenerative diseases and dementia disorders (such as Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia), polyneuropathies (such as Guillain-Barré syndrome, chronic inflammatory demyelinating polyradiculoneuropathy, multifocal motor neuropathy), plexopathies, CNS demyelination (such as multiple sclerosis, acute disseminated/haemorrhagic encephalomyelitis, and subacute sclerosing panencephalitis), neuromuscular disorders (such as myasthenia gravis and Lambert-Eaton syndrome), spinal diorders (such as tropical spastic paraparesis, and stiff-man syndrome), paraneoplastic syndromes (such as cerebellar degeneration and encephalomyelitis), CNS trauma, migraine and stroke.

(6) (other tissues and systemic disease) atherosclerosis, Acquired Immunodeficiency Syndrome (AIDS), lupus erythematosus; systemic lupus, erythematosus; Hashimoto's thyroiditis, type I diabetes, nephrotic syndrome, eosinophilia fascitis, hyper IgE syndrome, lepromatous leprosy, idiopathic thrombocytopenia pupura; post-operative adhesions, sepsis and ischemic/reperfusion injury in the heart, brain, peripheral limbs hepatitis (alcoholic, steatohepatitis and chronic viral), glomerulonephritis, renal impairment, chronic renal failure and other organs (7) (allograft rejection) acute and chronic following, for example, transplantation of kidney, heart, liver, lung, bone marrow, skin and cornea; and chronic graft versus host disease;

(8) Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof, as hereinbefore defined in the manufacture of a medicament for use in therapy in combination with drugs used to treat asthma and rhinitis (such as inhaled and oral steroids, inhaled β2-receptor agonists and oral leukotriene receptor antagonists).

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt, solvate or prodrug thereof, as hereinbefore defined.

For the above-mentioned therapeutic uses the dosage administered will, of course, vary with the compound employed, the mode of administration, the treatment desired and the disorder indicated.

The compound of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% Yow, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:
(i) the title and sub-titled compounds of the examples and methods were named using the ACD labs/name program (version 6.0) from Advanced Chemical Development Inc, Canada;
(ii) unless stated otherwise, reverse phase preparative HPLC was conducted using a Symmetry, NovaPak or Ex-Terra reverse phase silica column;
(iii) Flash column chromatography refers to normal phase silica chromatography
(iv) solvents were dried with $MgSO_4$ or $Na_2SO_4$
(v) Evaporations were carried out by rotary evaporation in vacuo and work-up procedures were carried out after removal of residual solids such as drying agents by filtration;
(vi) Unless otherwise stated, operations were carried out at ambient temperature, that is in the range 18-25° C. and under an atmosphere of an inert gas such as argon or nitrogen;
(vii) yields are given for illustration only and are not necessarily the maximum attainable;
(viii) the structures of the end-products of the formula (1) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;
(ix) intermediates were not generally fully characterised and purity was assessed by thin layer chromatography (TLC), high-performance liquid chromatography (HPLC), mass spectrometry (MS), infra-red (IR) or NMR analysis;
(x) mass spectra (MS): generally only ions which indicate the parent mass are reported when given, $^1H$ NMR data is quoted in the form of delta values for major diagnostic protons, given in parts per million (ppm) relative to tetramethylsilane (TMS) as an internal standard;
(xi) the following abbreviations are used:
EtOAc Ethylacetate
DMF N,N-Dimethyl formamide
NMP N-methylpyrrolidine
THF tetrahydrofuran
RT room temperature
TFA trifluoroacetic acid
MCPBA meta-chloroperbenzoic acid

EXAMPLE 1

3-[(4-chlorophenyl)sulfonyl]-2,5-dimethyl-1H-indol-1-acetic acid (a) 3-[(4-chlorophenyl)thio]-2,5-dimethyl-1H-indole To a solution of methylphenylhydrazine (7 g) in acetonitrile (100 ml) was added 1-[(4-chlorophenyl)thio]acetone (8.84 g) and water (10 ml). The mixture was stirred at room temperature overnight. The reaction mixture was concentrated in vacuo and the residue dissolved in dichloromethane. The solution was washed with sodium hydrogen carbonate, brine, dried ($MgSO_4$) and concentrated in vacuo. The residue was recrystallised (methanol) to give the sub-title compound (6 g).
MS: APCI+ [M+H] 288

(b) 3-[(4-chlorophenyl)sulfonyl]-2,5-dimethyl-1H-indole

The product of example 1 step (a) (1.85 g) was dissolved in dichloromethane (20 ml) at 0° C., to this solution MCPBA (2.85 g) was added and stirred for 2 hours. The reaction mixture was then washed with sodium carbonate solution, the organic extracts were dried with $MgSO_4$. Purification by Flash column chromatography (35% EtOAc/hexane as eluent) gave of the sub-title compound (1.27 g).
MS: ES+ [M+H] 320

(c) 3-[(4-chlorophenyl)sulfonyl]-2,5-dimethyl-1H-indol-1-acetic acid ethyl ester The product of step (b) (1.27 g) was dissolved in THF (20 ml) at ° C. and NaH (0.115 g, 60% dispersion in oil) was added and stirred for 30 min. Ethylbromoacetate (0.66 ml) was then added and stirred for 1 h at room temperature. Ethanol was added to quench the reaction, the solvent was removed and the product washed with water and extracted with EtOAc. Purification by Flash column chromatography (30% EtOAc/hexane as eluent) gave the sub-title compound (0.716 g).
MS: ES+ [M+H] 406

(d) 3-[(4-chlorophenyl)sulfonyl]-2,5-dimethyl-1H-indol-1-acetic acid

The product of step (c) was dissolved in ethanol (10 ml) and 10% NaOH (aq) (10 ml) was added and stirred for 1 h. The reaction mixture was then acidified with HCl (aq), and extracted with EtOAc. Purification by solid phase extraction using $NH_2$ sorbent (2 g), eluting with acetonitrile followed by 10% acetic acid/acetonitrile, gave the title compound (0.301 g).
MS: ES– [M–H] 376
$^1$H NMR (DMSO) δ 2.42 (3H, s), 2.62 (3H, s), 4.68 (2H, s), 7.01 (1H, dd), 7.29-7.33 (1H, m), 7.58-7.62 (2H, m), 7.65-7.69 (1H, m), 7.87-7.93 (2H, m).

EXAMPLE 2

5-chloro-3-[(4-chlorophenyl)sulfonyl]-2-methyl-1H-indole-1-acetic acid a) 5-chloro-3-[4(-chlorophenyl)sulfonyl]-2-methyl-1H-indole To a suspension of (4-chlorophenyl)-hydrazine hydrochloride (2 g) in acetic acid (30 ml) was added 1-[(4-chlorophenyl)thio]-acetone (2.24 g), acetonitrile (20 ml) and water (10 ml). The mixture was stirred at room temperature overnight. The reaction mixture was concentrated in vacuo and the residue suspended in EtOAc, washed with sodium hydrogen carbonate solution, brine, dried ($MgSO_4$) and concentrated in vacuo. The residue was dissolved in acetic acid (20 ml) and heated to 80° C. overnight. The reaction mixture was poured into water, basified using NaOH and the organics extracted into EtOAc. The EtOAc was washed with brine, dried ($MgSO_4$) and concentrated in vacuo. Purification by Flash column chromatography (20% EtOAc/hexane as eluent) gave the sub-title compound (2.2 g).
$^1$H NMR ($CDCl_3$) δ 8.31 (1H, s), 7.48 (1H, d), 7.26 (2H, m), 7.13 (3H, m), 6.93 (2H, m), 2.51 (3H, s).

b) 5-chloro-3-[(4-chlorophenyl)thio]-2-methyl-1H-indole-1-acetic acid, methyl ester To a solution of the product of step (a) (0.2 g) in THF (5 ml) was added 1M sodium bis(trimethylsilyl)amide solution in THF (0.65 ml). The mixture was stirred for 30 min before bromo-acetic acid, methyl ester (62 µl) was added, the reaction was stirred at room temperature overnight. A further 0.3 ml of 1.0M sodium bis(trimethylsilyl)amide solution in THF and 30 µl of methyl bromoacetate was added to the mixture and was stirred for a further 3 h. The mixture was then adsorbed onto silica and purified by Flash column chromatography (14% EtOAc/hexane as eluent) to give sub-title compound (0.21 g).
$^1$H NMR ($CDCl_3$) d 7.52 (1H, d), 7.27 (1H, d), 7.20-7.10 (3H, m), 6.97-6.89 (2H, m), 4.80 (2H, d), 3.79 (3H, d), 2.47 (3H, d).

c) 5-chloro-3-[(4-chlorophenyl)sulfonyl]-2-methyl-1H-indole-1-acetic acid, methyl ester To a solution of the product of step (b) (0.1 g) in dichloromethane (5 ml) was added MCPBA (121 mg). The mixture was stirred at room temperature overnight. The reaction was diluted with dichloromethane (10 ml), washed with sodium hydrogen carbonate solution, brine, dried ($MgSO_4$) and concentrated in vacuo to give sub-title compound (0.1 g). Used in step (d) without further purification and characterisation.

d) 5-chloro-3-[(4-chlorophenyl)sulfonyl]-2-methyl-1H-indole-1-acetic acid

To a solution of the product from step (c) (0.09 g) in THF (5 ml) was added a 1.25 M solution of NaOH(aq) (0.25 ml). The reaction was stirred overnight at room temperature. The reaction mixture was concentrated in vacuo and the residue dissolved/suspended in water. The pH was adjusted to 2 using dilute HCl (aq) and the solid which precipitated was isolated by filtration, dried under vacuum at 40° C. to give the title compound.
MS: APCI– [M–H] 398
$^1$H NMR (DMSO) δ 7.94 (2H, m), 7.89 (1H, d), 7.67-7.62 (3H, m), 7.29 (1H, m), 5.12 (2H, s), 2.63 (3H, s).

EXAMPLE 3

6-chloro-3-[(4-chlorophenyl)sulfonyl]-2-methyl-1H-indole-1-acetic acid a) 6-chloro-3-[4(-chlorophenyl)thio]-2-methyl-1H-indole The subtitle compound was prepared by the method of example 2 part (a) using (3-chlorophenyl)-hydrazine hydrochloride. Product purified using Flash column chromatography (10% EtOAc/hexane as eluent).
$^1$H NMR ($CDCl_3$) δ 8.27 (1H, s) 7.39 (1H, d) 7.34 (1H, d), 7.10 (3H, m), 6.92 (2H, m), 2.50 (3H, s).

b) 6-chloro-3-[(4-chlorophenyl)thio]-2-methyl-1H-indole-1-acetic acid, methyl ester The sub-title compound was prepared by the method of example 2 part (b) using the product from part (a).
$^1$H NMR ($CDCl_3$) δ 7.43 (1H, d), 7.27-7.25 (1H, m), 7.14-7.09 (3H, m), 6.92 (2H, dd), 4.85 (2H, s), 3.80 (3H, d), 2.46 (3H, d).

c) 6-chloro-3-[(4-chlorophenyl)sulfonyl]-2-methyl-1H-indole-1-acetic acid, methyl ester The subtitle compound was prepared by the method of example 2 part (c) using the product from part (b). Used in step (d) without further purification or characterisation.

d) 6-chloro-3-[(4-chlorophenyl)sulfonyl]-2-methyl-1H-indole-1-acetic acid

The title compound was prepared by the method of example 2 part (d) using the product from part (c).
MS: ES– [M–H] 398
$^1$H NMR (DMSO) δ 7.94-7.89 (3H, m), 7.80 (1H, d) 7.64 (2H, m), 7.27 (1H, m), 5.13 (2H,s), 2.63 (3H, s).

EXAMPLE 4

7-chloro-3-[(4-chlorophenyl)sulfonyl]-2-methyl-1H-indole-1-acetic acid a) 7-chloro-3-[4(-chlorophenyl)thio]-2-methyl-1H-indole

The subtitle compound was prepared by the method of example 2 part (a) using (2-chlorophenyl)-hydrazine hydrochloride.
$^1$H NMR (CDCl$_3$) δ 8.48 (1H, s) 7.40 (1H, d), 7.19 (1H, m) 7.13-7.11 (2H, m), 7.06 (1H, t), 6.96-6.92 (2H, m), 2.55 (3H, s).

b) 7-chloro-3-[(4-chlorophenyl)thio]-2-methyl-1H-indole-1-acetic acid, methyl ester The sub-title compound was prepared by the method of example 2 part (b) using the product from step (a).
$^1$H NMR(CDCl$_3$) δ 7.44 (1H, d), 7.18-7.09 (3H, m), 7.03 (1H, td), 6.92 (2H, dd), 5.37 (2H, d), 3.81 (3H, d), 2.46 (3H, d).

c) 7-chloro-3-[(4-chlorophenyl)sulfonyl]-2-methyl-1H-indole-1-acetic acid, methyl ester The sub-title compound was prepared by the method of example 2 part (c) using the product from step (b). Used in step (d) without further purification or characterisation.

d) 7-chloro-3-[(4-chlorophenyl)sulfonyl]-2-methyl-1H-indole-1-acetic acid

The title compound was prepared by the method of example 2 part (d) using the product from part (c).
MS: ES– [M–H] 398
$^1$H NMR (DMSO) δ 7.96-7.93 (3H, m), 7.65 (2H, m), 7.30 (1H, m), 7.22 (1H, t) 5.32 (2H, s), 2.70 (3H, s).

EXAMPLE 5

5-chloro-3-[(4-chlorophenyl)sulfonyl]-4-cyano-2-methyl-1H-indole-1-acetic acid a) 3-[(4-chlorophenyl)thio]-2,5-dimethyl-1H-indole-4-carbonitrile

A stirred solution of 1-[(4-chlorophenyl)thio]-acetone (6.14 g) in dry dichloromethane (150 ml) at −78° C. was treated with sulphuryl chloride (2.25 ml). After 30 min a prepared solution of N,N,N',N'-tetramethyl-1,8-naphthalenediamine (6.01 g) and 5-amino-2-chloro-benzonitrile (3.89 g) in dry dicholoromethane (80 ml) was added dropwise over 30 min. The mixture was stirred for a further 2 h, after which triethylamine (4.26 ml) was added and the reaction allowed to reach room temperature. The reaction mixture was diluted with dichloromethane (200 ml), washed with water, 1N HCl and brine. The organic phase was dried (MgSO$_4$), evaporated in vacuo, and the residue purified by flash column chromatography eluting with isohexane and ethyl acetate (1:1) to give the sub-title compound (1 g), and the regioisomer (600 mg) used in example 6 below.
$^1$H NMR CDCl$_3$: δ 12.52 (s,1H), 7.74 (d, 1H), 7.38 (dd, 1H), 7.29 (m, 2H), 6.97 (m, 2H), 3.29 (s, 3H).

b) 3-[(4-chlorophenyl)thio]-4-cyano-2,5-dimethyl-1H-indole-1-acetic acid, methyl ester The sub-title compound was prepared by the method of example 1 part (c) using the product of part (a).
$^1$H NMR CDCl$_3$: δ 7.37 (1H, d), 7.30 (1H, d), 7.18-7.13 (2H, m), 7.00-6.96 (2H, m), 4.92 (2H, m), 3.80 (3H, m), 2.55 (3H, s).

(c) 5-chloro-3-[(4-chlorophenyl)sulfonyl]-4-cyano-2-methyl-1H-indole-1-acetic acid, methyl ester The sub-title compound was prepared by the method if example 1 part (b) from the product of part (b).

(d) 5-Chloro-3-[(4-chlorophenyl)sulfonyl]-4-cyano-2-methyl-1H-indole-1-acetic acid The title compound was prepared by the method of example 1 part (d) using the product of part (c).
$^1$H NMR DMSO: δ 2.81(3H, s), 5.29 (2H, s), 7.62 (1H, s), 7.7 (2H, m), 7.98(2H, m) and 8.08(1H, d).
MS: APCI+ [M+H] 422

EXAMPLE 6

5-chloro-3-[(4-chlorophenyl)sulfonyl]-6-cyano-2-methyl-1H-indole-1-acetic acid a) 5-chloro-3-[(4-chlorophenyl)sulfonyl]-2-methyl-1H-indole-6-carbonitrile

Obtained from example 5 part (a)
$^1$H NMR CDCl$_3$: δ 8.68 (1H, s), 7.69 (1H, s), 7.61 (1H, s), 7.15 (2H, dt), 6.91 (2H, dt), 2.57 (3H, s).

b) 5-chloro-3-[(4-chlorophenyl)sulfonyl]-6-cyano-2-methyl-1H-indole-1-acetic acid Prepared by the method of example 2 part (d) to give the title compound as a white solid.
$^1$H NMR DMSO: δ 8.42 (1H, s), 7.59 (1H, s), 7.3 (2H, dt), 6.99 (2H, dt), 5.24 (2H, s), 2.46 (3H, s).
M.pt 256-258° C.
MS: APCI [M–H] 389

EXAMPLE 7

3-[(4-chlorophenyl)sulfinyl]-2,5-dimethyl-1H-indole-1-acetic acid a) 3-[(4-chlorophenyl)sulfinyl]-2,5-dimethyl-1H-indole-1-acetic acid, ethyl ester MCPBA (1.07 g) was added to a solution of example 1 part a) (1.79 g) in dichloromethane (20 ml) at 0° C. The reaction mixture was stirred for 1 h, after which further mCPBA (53 mg) was added and stirred for a further 30 min. The reaction mixture was allowed to reach room temperature and the subtitle compound was obtained as a white solid after filtration (0.68 g). Used directly in the next step without further purification.

b) 3-[(4-chlorophenyl)sulfinyl]-2,5-dimethyl-1H-indole-1-acetic acid

NaH (0.13 g, 60% dispersion in mineral oil) was added to the product from part (a) (0.685 g) in THF at 0° C. The reaction mixture was stirred for 30 min and then ethyl bromoacetate (0.26 ml) was added and the mixture stirred for 1 h. Ethanol was added and then concentrated in vacuo. The product was extracted with EtOAc, dried (MgSO$_4$) and concentrated in vacuo to give a white solid (761 mg). The solid was dissolved in ethanol (15 ml), NaOH (10% solution, 5 ml) and then the solution stirred overnight. The reaction mixture was acidified (dilute HCl) and extracted with EtOAC. The organic phase was dried (MgSO$_4$) and concentrated in vacuo. The product was purified with amine resin, eluting with MeCN and then 5% acetic acid in MeCN to give the title compound (60 mg).
$^1$H NMR DMSO: δ 7.61 (4H, s), 7.2-7.25 (1H, m), 6.88-6.91 (1H, m), 6.88-6.86 (1H, m), 4.43 (2H, s), 2.57 (3H, s) and 2.21 (3H, s).

EXAMPLE 8

3-[(4-chlorophenyl)sulfonyl]-4-(ethylsulfonyl)-7-methoxy-2-methyl-1H-indole-1-acetic acid a) 3-[(4-chlorophenyl)thio]-4-(ethylsulfonyl)$_7$-methoxy-2-methyl-1H-indole Prepared by the method of example 5 part (a) from 5-(ethylsulfonyl)-2-methoxy-benzenamine.
$^1$H NMR CDCl$_3$: δ 9.00 (1H, s), 7.91 (1H, d), 7.12 (2H, dd), 6.86 (2H, m), 6.73 (1H,d), 4.05 (3H, s), 3.46 (2H,q), 2.46 (3H, s) and 1.16 (3H, t).

b) 3-[(4-chlorophenyl)thio]-4-(ethylsulfonyl)-7-methoxy-2-methyl-1H-indole-1-acetic acid, methyl ester Prepared by the method of example 5 part (b), using the product of step (a.)
$^1$H NMR CDCl$_3$: δ 7.92 (1H, d), 7.13 (2H, dt), 6.85 (2H, dt), 6.73 (1H,d), 5.27 (2H,s), 3.98 (3H, s), 3.79 (3H, s), 3.48 (2H, q), 2.38 (3H,s) and 1.18 (3H, t).

c) 3-[(4-chlorophenyl)sulfonyl]-4-(ethylsulfonyl)-7-methoxy-2-methyl-1H-indole-1-acetic acid, methyl ester Prepared by the method of example 5 part (c) using the product of step (b).
MS: ES+ [M+H] 435 d) 3-[(4-chlorophenyl)sulfonyl]-4-(ethylsulfonyl)-7-methoxy-2-methyl-1H-indole-1-acetic acid Prepared by the method of example 5 part (d) using the product of step (c).
$^1$H NMR DMSO: δ 7.79 (1H, d), 7.73 (2H, d), 7.58 (2H, d), 7.04 (1H, d), 5.07 (2H, s), 3.95 (3H, s), 3.58 (2H, q), 2.66 (3H,s) and 1.23 (3H, t).

EXAMPLE 9

3-[(4-chlorophenyl)sulfinyl]-5-cyano-2-methyl-1H-indole-1-acetic acid a) 3-[(4-chlorophenyl)thio]-5-cyano-2-methyl-1H-indole

To a stirred solution of 4-aminobenzonitrile (5 g) in dichloromethane (150 ml) cooled to −70° C. was added t-butyl hypochlorite (4.6 g) dropwise over 5 mins. The reaction was stirred for 10 mins before 1-[4-chlorophenyl)thio]-2-propanone (8.49 g) was added as a solution in dichloromethane (20 ml). After 1 h triethylamine (5.9 ml) was added and the reaction allowed to warm to room temperature. The reaction was diluted with dichloromethane, washed with HCl (aq), brine, dried over MgSO$_4$, and concentrated in vacuo to give a brown solid. Purification by recystallisation from Methanol gave the subtitle compound (7.5 g).
$^1$H NMR (CDCl$_3$) δ 8.61 (s, 1H), 7.84 (s, 1H), 7.44 (dd, 1H), 7.41 (d, 1H), 7.19-7.08 (m, 2H), 6.93 (dd, 2H), 2.56 (s, 3H).

b) 3-[(4-chlorophenyl)thio]-5-cyano-2-methyl-1H-indole-acetic acid, ethyl ester The subtitle compound was prepared by the method of example 5 part (b) using the product from part (a) and ethyl bromoacetate. The product was used without further characterisation in part (c).

c) 3-[(4-chlorophenyl)sulfinyl]-5-cyano-2-methyl-1H-indole-1-acetic acid, methyl ester mCPBA (128 mg) was added to the product of part (b) (200 mg) in dichloromethane (10 ml), and stirred overnight. The solution was washed (NaHCO$_3$), brine, then dried (MgSO$_4$) and concentrated in vacuo to give the subtitle compound as a white solid (170 mg).

d) 3-[(4-chlorophenyl)sulfinyl]-5-cyano-2-methyl-1H-indole-1-acetic acid

The title compound was prepared by the method of example 5 part (d) using the product of step (c).
$^1$H NMR (DMSO) δ 7.69-7.57 (m, 6H), 7.51 (dd, 1H), 4.85 (dd, 2H) and 2.63 (s, 3H)

EXAMPLE 10

3-[(4-chlorophenyl)sulfonyl]-5-cyano-2-methyl-1H-indole-1-acetic acid a) 1H-indole-1-acetic acid, 3-[(4-chlorophenyl)sulfonyl]-5-cyano-2-methyl-1H-indole-1-acetic acid, methyl ester The sub-title compound was prepared by the method of example 5 part (c) using the product of example 9 part (b).
$^1$H NMR (DMSO) δ 8.35 (d, 1H), 8.03 (dt, 2H), 7.82 (d, 1H), 7.71-7.62 (m, 3H), 5.32 (s, 2H), 4.15 (q, 2), 2.67 (s, 3H) and 1.18 (td, 3H)

b) 1H-indole-1-acetic acid, 3-[(4-chlorophenyl)sulfonyl]-5-cyano-2-methyl-1H-indole-1-acetic acid The title compound was prepared by the method of example 5 part (d) using the product of step (a)

¹H NMR (DMSO) δ 8.35 (d, 1H), 8.05-8.01 (m, 2H), 7.82 (d, 1H), 7.69-7.63 (m, 3H), 5.20 (s, 2H) and 2.67 (s, 3H).

EXAMPLE 11

Sodium 5-chloro-3-[(4-chlorophenyl)sulfonyl]-2-methyl-1H-indole-1-acetate

Sodium hydroxide (1M, 4.3 ml) was added to a solution of the product of example 1 part (c) (1.75 g) in THF (60 ml). The reaction mixture was stirred overnight and then concentrated in vacuo. The residue was recrystallised from water to give the title compound as a white solid.

¹H NMR (DMSO) δ 7.89 (dd, 2H), 7.66 (d, 1H), 7.61 (m, 2H), 7.26(d, 1H), 6.99 (1H, dd), 4.39(s, 2H), 2.59 (s, 3H) and 2.4(s, 3H).

EXAMPLE 12

4-chloro-3-[(4-chlorophenyl)sulfonyl]-2-methyl-1H-indole-1-acetic acid

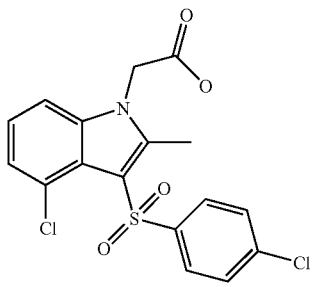

a) 4-chloro-3-[4(-chlorophenyl)thio]-2-methyl-1H-indole

The subtitle compound was prepared by the method of example 2 part (a) using (3-chlorophenyl)-hydrazine hydrochloride. Product purified using Flash column chromatography (10% EtOAc/hexane as eluent).

¹H NMR (CDCl₃) δ 8.38 (1H, s), 7.27-7.24 (2H, m), 7.15-7.11 (2H, m), 7.09-7.08 (1H, m), 6.96 (2H, dt), 2.52 (3H, s)

b) 4-chloro-3-[(4-chlorophenyl)sulfonyl]-2-methyl-1H-indole

The subtitle compound was prepared by the method of example 1 part (b) using the product from part (a). Product was purified using Flash column chromatography (33% EtOAc/hexane as eluent).

¹H NMR (DMSO) δ 12.57 (1H, s), 7.83 (2H, dt), 7.60 (2H, dt), 7.41 (1H, dd), 7.18-7.08 (2H, m), 2.80 (3H, s)

c) 4-chloro-3-[(4-chlorophenyl)sulfonyl]-2-methyl-1H-indole-1-acetic acid ethyl ester The subtitle compound was prepared by the method of example 1 part (c) using the product from part (b). Product was purified using Flash column chromatography (33% EtOAc/hexane as eluent).

¹H NMR (DMSO) δ 7.80 (2H, dt), 7.63 (3H, m), 7.25-7.16 (2H, m), 5.36 (2H, s), 4.20, (2H, q), 2.81 (3H, s), 1.23 (3H, t).

d) 4-chloro-3-[(chlorophenyl)sulfonyl]-2-methyl-1H-indole-1-acetic acid

The title compound was prepared by the method of example 2 part (d) using the product from part (c). Product was purified using reverse phase preparative HPLC (eluent MeCN/NH₃(aq)).

¹H NMR (DMSO) δ 7.79 (2H, dt), 7.62 (2H, dt), 7.52 (1H, dd), 7.19-7.11 (2H, m), 4.84 (2H, s), 2.78 (3H, s). APCI–(M–H) 395.

EXAMPLE 13

3-[(4-methoxyphenyl)sulfonyl]-2,5-dimethyl-1H-indol-1-acetic acid

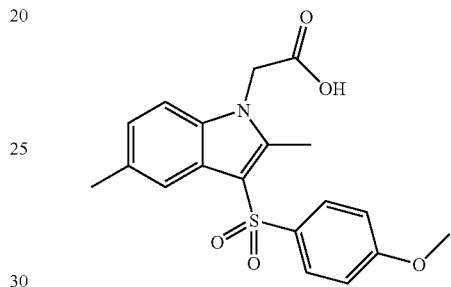

a) 2,5-dimethyl-1H-indol-1-acetic acid

60% sodium hydride/oil (0.64 g) was added to a solution of 2,5-dimethyl-1H-indole (2.0 g) in DMF (15 ml). After 15 min ethyl bromoacetate (2.7 ml) was added quickly and the reaction stirred for 20 min. The mixture was quenched with 1% aqueous acetic acid (100 ml), extracted with ethyl acetate (2×100 ml) and washed with water (2×50 ml) and brine (20 ml). The extracts were dried (MgSO₄), filtered and evaporated in vacuo to yield a brown solid. The solid was dissolved in EtOH (20 ml) and aqueous sodium hydroxide (1M,10 ml) added. After 1 h the solution was adjusted to pH6 with aqueous hydrochloric acid (1M,~10 ml), and then evaporated in vacuo. The residue was purified by flash column chromatography (gradient 1-10% methanol in dichloromethane). The sub-title compound was obtained as a red/brown solid (1.3 g).

MS: APCI+ [M+H] 204

¹H NMR δ$_{(DMSO)}$ 7.22-7.17 (2H, m), 6.85 (1H, d), 6.11 (1H, s), 4.87 (2H, s), 2.34 (3H, s), 2.30 (3H, s)

b) 3-[(4-methoxyphenyl)thio]-2,5-dimethyl-1H-indol-1-acetic acid, ammonium salt Iodine (0.51 g) was added to a solution of 4-methoxybenzenethiol (0.25 g) and the product from example 13 step a) (0.2 g) in DMF (5 ml). After 1 h the solution was purified by reverse phase HPLC. The solvent was evaporated in vacuo and the oily residue treated with ether to give a solid. Filtered off and dried to yield the title compound as a white solid (0.27 g).

MS (APCI–) 340 [(M–NH₄)–H]⁻

¹H NMR δ$_{(DMSO)}$ 7.24 (1H, d), 7.15 (1H, s), 6.95 (2H, d), 6.90 (1H, d), 6.78 (2H, d), 4.60 (2H, s), 3.66 (3H, s), 2.38 (3H, s), 2.33 (3H, s)

c) 3-[(4-methoxyphenyl)sulfonyl]-2,5-Dimethyl-1H-indol-1-acetic acid

3-Chlorobenzenecarboperoxoic acid (0.44 g) was added to a solution of the product from example 13 step ii) (0.2 g) in acetonitrile (4 ml). The reaction was stirred for 1 h, 1M aqueous sodium thiosulphate (2 ml) added and stirred for a further 15 min. The mixture was filtered, purified by reverse phase HPLC and evaporated in vacuo to yield the title compound as a white solid (98 mg).

MS: APCI– [M−H] 372

$^1$H NMR $\delta_{(DMSO)}$ 7.83 (2H, d), 7.69 (1H, s), 7.33 (1H, d), 7.09-6.98 (1H, m), 7.06 (2H, d), 4.79 (3H, s), 3.78 (3H, s), 2.59 (3H, s), 2.40 (3H, s)

EXAMPLE 14

3-[(3-methoxyphenyl)sulfonyl]-2,5-dimethyl-1H-indol-1-acetic acid

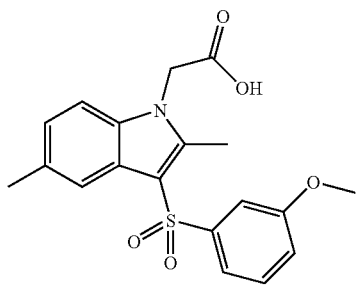

a) 3-[(3-methoxyphenyl)thio]-2,5-dimethyl-1H-indol-1-acetic acid

Iodine (0.51 g) was added to a solution of 3-methoxylbenzenethiol (0.25 g) and the product from example 13 step i) (0.2 g) in DMF (5 ml). After 1 h the solution was purified by reverse phase HPLC. The solvent was evaporated in vacuo and the oily residue treated with ether to give a solid. Filtered off and dried to yield the title compound as a white solid (0.22 g).

MS: APCI– [M−H] 340

$^1$H NMR $\delta_{(DMSO)}$ 7.40 (1H, d), 7.16 (1H, s), 7.11 (1H, t), 6.98 (1H, d), 6.63 (1H, d), 6.55 (1H, d), 6.45 (1H, s), 5.08 (2H, s), 3.61 (3H, s), 2.39 (3H, s), 2.34 (3H, s)

b) 3-[(3-methoxyphenyl)sulfonyl]-2,5-dimethyl-1H-indol-1-acetic acid

3-Chlorobenzenecarboperoxoic acid (0.4 g) was added to a solution of the product from example 14 step i) (0.18 g) in acetonitrile (4 ml). The reaction was stirred for 1 h, 1M aqueous sodium thiosulphate (2 ml) added and stirred for a further 15 min. The mixture was filtered, purified by reverse phase HPLC and evaporated in vacuo to yield the title compound as a white solid (70 mg).

MS: APCI– [M−H] 372

$^1$H NMR $\delta_{(DMSO)}$ 7.69 (1H, s), 7.48-7.43 (2H, m), 7.36-7.32 (1H, m), 7.31 (1H, d), 7.18-7.11 (1H, m), 7.01 (1H, d), 4.66 (2H, s), 3.78 (3H, s), 2.61 (3H, s), 2.40 (3H, s)

EXAMPLE 15

3-[(2-Chlorophenyl)sulfonyl]-2,5-dimethyl-1H-indol-1-acetic acid

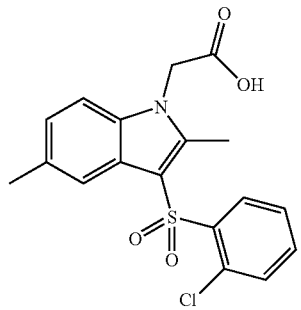

a) 3-[(2-Chlorophenyl)thio]-2,5-dimethyl-1H-indol-1-acetic acid, sodium salt Iodine (0.22 g) was added to a solution of 2-chlorobenzenethiol (0.13 g) and the product from example 13 step a) (015 g) in EtOH (5 ml). After 1 h the solution was purified by reverse phase HPLC. The solvent was evaporated in vacuo to yield the product as a colourless oil. The oil was then dissolved in MeOH (10 ml) treated with aqueous sodium hydroxide (1M,0.52 ml) and evaporated in vacuo to yield the sodium salt as a white solid (0.13 g).

MS: APCI– [M−Na] 344

$^1$H NMR $\delta_{(DMSO)}$ 7.28-7.15 (2H, m), 7.13-7.06 (2H, m), 6.97-6.88 (3H, m), 4.42 (2H, s), 2.36 (3H, s), 2.33 (3H, s)

b) 3-[(2-Chlorophenyl)sulfonyl]-2,5-dimethyl-1H-indol-1-acetic acid

3-Chlorobenzenecarboperoxoic acid (0.14 g) was added to a solution of the product from example 15 step a) (0.07 g) in acetonitrile (2 ml) and water (0.5 ml). The reaction was stirred for 1 h, 1M aqueous sodium thiosulphate (2 ml) added and stirred for a further 15 min. The mixture was filtered, purified by reverse phase HPLC and evaporated in vacuo to yield the title compound as a white solid (11 mg).

MS APCI– [M−H]⁻ 376

$^1$H NMR $\delta_{(DMSO)}$ 8.32-8.25 (1H, m), 7.64-7.52 (3H, m), 7.39 (1H, s), 7.34 (1H, d), 6.99 (1H, d), 4.73 (2H, s), 2.59 (3H, s), 2.32 (3H, s)

EXAMPLE 16

3-[(3-Chlorophenyl)sulfonyl]-2,5-dimethyl-1H-indol-1-acetic acid

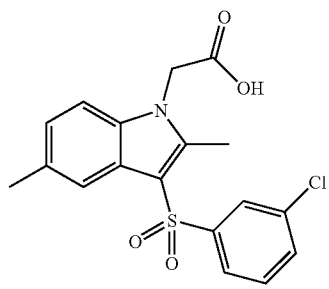

a) 3-[(3-Chlorophenyl)thio]-2,5-dimethyl-1H-indol-1-acetic acid, sodium salt Iodine (0.29 g) was added to a solution of 3-chlorobenzenethiol (0.175 g) and the product from example 13 step a) (0.2 g) in EtOH (5 ml). After 1 h the solution was purified by reverse phase HPLC. The solvent was evaporated in vacuo to yield the product as a colourless oil. The oil was then dissolved in MeOH (10 ml) treated with aqueous sodium hydroxide (1M, 0.52 ml) and evaporated in vacuo to yield the sodium salt as a white solid (0.19 g).

MS (APCI−) 344 [(M−Na)−H]⁻

$^1$H NMR $\delta_{(DMSO)}$ 7.28-7.15 (2H, m), 7.13-7.06 (2H, m), 6.97-6.88 (3H, m), 4.42 (2H, s), 2.36 (3H, s), 2.33 (3H, s)

b) 3-[(3-Chlorophenyl)sulfonyl]-2,5-dimethyl-1H-indol-1-acetic acid

3-Chlorobenzenecarboperoxoic acid (0.32 g) was added to a solution of the product from example 16 step a) (0.16 g) in acetonitrile (4 ml) and water (1 ml). The reaction was stirred for 1 h, 1M aqueous sodium thiosulphate (2 ml) added and stirred for a further 15 min. The mixture was filtered, purified by reverse phase HPLC and evaporated in vacuo to yield the title compound as a white solid (65 mg).

MS APCI− [M−H]⁻ 376

$^1$H NMR $\delta_{(DMSO)}$ 7.87 (2H, d), 7.68 (2H, d), 7.63-7.56 (1H, m), 7.36 (1H, d), 7.04 (1H, d), 4.79 (2H, s), 2.62 (3H, s), 2.41 (3H, s)

EXAMPLE 17

3-[(4-Cyanophenyl)sulfonyl]-2,5-dimethyl-1H-indole-1-acetic acid

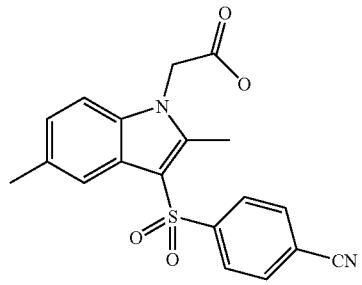

a) 3-[(4-Cyanophenyl)thio]-2,5-dimethyl-1H-indol-1-acetic acid, ammonium salt Iodine (0.51 g) was added to a solution of 4-cyanobenzenethiol (0.27 g) and the product from example 13 step a) (0.2 g) in DMF (5 ml). After 1 h the solution was purified by reverse phase HPLC. The solvent was evaporated in vacuo and the oily residue treated with ether to give a solid. Filtered off and dried to yield the title compound as a white solid (0.25 g).

MS APCI− [(M−NH₄)−H]⁻ 334

$^1$H NMR $\delta_{(DMSO)}$ 7.62 (2H, d), 7.35 (1H, d), 7.10 (1H, s), 7.08 (2H, d), 6.97 (1H, d), 4.80 (2H, s), 2.36 (3H, s), 2.32 (3H, s)

b) 3-[(4-Cyanophenyl)sulfonyl]-2,5-dimethyl-1H-indole-1-acetic acid

3-Chlorobenzenecarboperoxoic acid (0.44 g) was added to a solution of the product from example 17 step a) (0.21 g) in acetonitrile (4 ml). The reaction was stirred for 1 h, 1M aqueous sodium thiosulphate (2 ml) added and stirred for a further 15 min. The mixture was filtered, purified by reverse phase HPLC and evaporated in vacuo to yield the title compound as a white solid (58 mg).

MS (APCI−) [M−H]⁻ 367

$^1$H NMR $\delta_{(DMSO)}$ 8.04 (4H, dd), 7.69 (1H, s), 7.36 (1H, d), 7.04 (1H, d), 4.76 (2H, s), 2.61 (3H, s), 2.41 (3H, s)

EXAMPLE 18

3-[(2-methylphenyl)sulfonyl]-2,5-Dimethyl-1H-indol-1-acetic acid

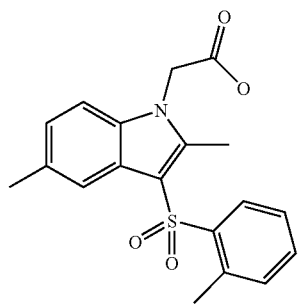

a) 3-[(2-methylphenyl)thio]-2,5-dimethyl-1H-indol-1-acetic acid, ammonium salt Iodine (0.29 g) was added to a solution of 2-methylbenzenethiol (0.16 g) and the product from example 13 step a) (0.2 g) in DMF (5 ml). After 1 h the solution was purified by reverse phase HPLC. The solvent was evaporated in vacuo and the oily residue treated with ether to give a solid. Filtered off and dried to yield the title compound as a white solid (0.19 g).

MS APCI− [(M−NH)−H]⁻ 324

$^1$H NMR $\delta_{(DMSO)}$ 7.24 (1H, d), 7.15 (1H, d), 7.07 (1H, s), 6.97-6.86 (3H, m), 6.47 (1H, d), 4.49 (2H, s), 2.42 (3H, s), 2.33 (3H, s), 2.31 (3H, s)

b) 3-[(2-methylphenyl)sulfonyl]-2,5-Dimethyl-1H-indol-1-acetic acid

3-Chlorobenzenecarboperoxoic acid (0.32 g) was added to a solution of the product from example 18 step a) (0.14 g) in acetonitrile (4 ml). The reaction was stirred for 1 h, 1M aqueous sodium thiosulphate (2 ml) added and stirred for a further 15 min. The mixture was filtered, purified by reverse phase HPLC and evaporated in vacuo to yield the title compound as a white solid (65 mg).

MS APCI− [M−H]⁻ 356

$^1$H NMR $\delta_{(DMSO)}$ 8.05 (1H, d), 7.54-7.40 (2H, m), 7.44 (1H, s), 7.40 (1H, d), 7.31 (1H, d), 7.01 (1H, d), 4.94 (2H, s), 2.54 (3H, s), 2.38 (3H, s), 2.33 (3H, s)

EXAMPLE 19

3-[(2-ethylphenyl)sulfonyl]-2,5-dimethyl-1H-indol-1-acetic acid

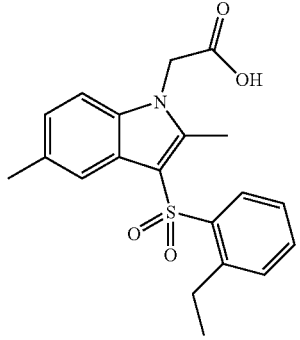

a) 3-[(2-ethylphenyl)thio]-2,5-dimethyl-1H-indol-1-acetic acid, ammonium salt Iodine (0.44 g) was added to a solution of 2-ethylbenzenethiol (0.32 g) and the product from example 13 step a) (0.2 g) in DMF (5 ml). After 1 h the solution was purified by reverse phase HPLC. The solvent was evaporated in vacuo and the oily residue treated with ether to give a solid. Filtered off and dried to yield the title compound as a white solid (0.18 g).

MS (APCI−) 338 [(M−NH$_4$)−H]$^-$
$^1$H NMR $\delta_{(DMSO)}$ 7.26 (1H, d), 7.16 (1H, d), 7.08 (1H, s), 7.01-6.85 (3H, m), 6.48 (1H, d), 4.57 (2H, s), 2.83 (2H, q), 2.34 (3H, s), 2.31 (3H, s), 1.31 (3H, t)

b) 3-[(2-ethylphenyl)sulfonyl]-2,5-dimethyl-1H-indol-1-acetic acid

3-Chlorobenzenecarboperoxoic acid (0.32 g) was added to a solution of the product from example 19 step a) (0.14 g) in acetonitrile (4 ml). The reaction was stirred for 1 h, 1M aqueous sodium thiosulphate (2 ml) added and stirred for a further 15 min. The mixture was filtered, purified by reverse phase HPLC and evaporated in vacuo to yield the title compound as a white solid (45 mg).

MS APCI− [M−H]$^-$ 370
$^1$H NMR $\delta_{(DMSO)}$ 7.95 (1H, d), 7.58-7.50 (1H, m), 7.47 (1H, s), 7.44-7.34 (3H, m), 7.00 (1H, d), 4.81 (2H, s), 2.87 (2H, q), 2.51 (3H, s), 2.33 (3H, s), 0.94 (3H, t)

EXAMPLE 20

3-[(4-chlorophenyl)sulfonyl]-2-methyl-4-nitro-1H-indole-1-acetic acid

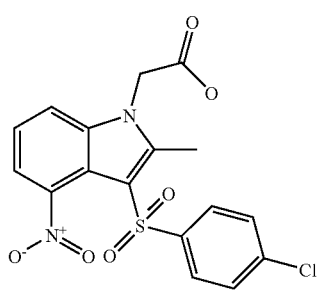

a) 3-[(4-chlorophenyl)thio]-2-methyl-4-nitro-1H-indole

To a stirred solution of 3-nitroaniline (8 g) in THF (700 ml) cooled to −78° C. was added t-butyl hypochlorite (6.3 g) dropwise over 5 minutes. The reaction was allowed to warm to −65° C. over 20 minutes before 1-[4-chlorophenyl)thio]-2-propanone (11.6 g) was added as a solution in tetrahydrofuran (20 ml). After 2 hours triethylamine (8.1 ml) was added and the reaction allowed to warm to room temperature. 2M HCl(aq) was added to the reaction mixture before concentration in vacuo. The residue was slurried in methanol and the solid which precipitated isolated by filtration to give the subtitle compound (5.8 g).

$^1$H NMR (DMSO) $\delta$12.55 (s, 1H), 7.76 (dd, 1H), 7.63 (dd, 1H), 7.31-7.22 (m, 3H), 6.91 (dd, 2H), 2.47 (s, 3H)

b) 3-[(4-chlorophenyl)thio]-2-methyl-4-nitro-1H-indole-acetic acid, ethyl ester To a stirred suspension of sodium hydride, 60% dispersion in mineral oil, (0.85 g) in THF (100 ml) was added the product from part (a) (5.6 g) as a solution in THF (50 ml). After stirring at room temperature for 30 minutes ethyl bromoacetate (2.3 ml) was added dropwise over 10 minutes. After 2 hours the reaction was concentrated in vacuo, the residue dissolved in ethyl acetate, washed with water, brine, dried (MgSO$_4$) and concentrated in vacuo. Recrystallisation from boiling ethanol gave the subtitle compound (5 g).

$^1$H NMR (DMSO) $\delta$7.97 (dd, 1H), 7.65 (dd, 1H), 7.35 (t, 1H), 7.26 (dt, 2H), 6.92 (dt, 2H), 5.40 (s, 2H), 4.19 (q, 2H), 2.45 (s, 3H), 1.22 (t, 3H).

c) 3-[(4-chlorophenyl)sulfonyl]-2-methyl-4nitro-1H-indole-acetic acid, ethyl ester To a solution of the product from part (b) (0.2 g) in dichloromethane (10 ml) was added MCPBA (0.245 g). After stirring overnight a further 20 ml of dichloromethane was added to the reaction before the mixture was washed with sodium hydrogen carbonate solution, brine, dried (MgSO$_4$) and concentrated in vacuo. The residue was used without further characterisation in step (d).

d) 3-[(4-chlorophenyl)sulfonyl]-2-methyl-4-nitro-1H-indole-acetic acid

The title compound was prepared by the method of example 2 part (d) using the product from part (c). Product was purified using reverse phase preparative HPLC (eluent MeCN/NH$_3$ (aq)).

$^1$H NMR (DMSO) $\delta$7.97 (1H, dd), 7.85 (2H, dt), 7.68 (2H, m), 7.65 (1H, d), 7.40 (1H, t), 5.10 (2H, s), 2.77 (3H, s). APCI− (M−H) 407

EXAMPLE 21

4-(Acetylamino)-3-[(4-chlorophenyl)sulfonyl]-2-methyl-1H-indole-1-acetic acid

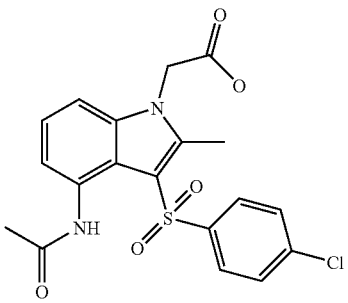

a) 4-amino-3-[(4-chlorophenyl)thio]-2-methyl-1H-indole-1-acetic acid, ethyl ester A suspension of the product from example 20 part (b) (2.25 g) in ethanol (170 ml) was stirred in the presence of 5% Pt/C (0.5 g) under 2 bar pressure of $H_2$. After stirring overnight the catalyst was removed by filtration and the filtrates concentrated in vacuo. Purification by flash column chromatography (14% EtOAc/hexane as eluent) gave the subtitle compound (1.4 g).

$^1$H NMR (DMSO) δ 7.30 (dd, 2H), 7.0 (dt, 2H), 6.85 (t, 1H), 6.68 (dd, 1H), 6.23 (dd, 1H), 5.33 (s, 2H), 5.09 (s, 2H), 4.16 (q, 2H), 2.33 (s, 3H), 1.21 (t, 3H).

3-[(4-chlorophenyl)thio]-4-(ethylamino)-2-methyl-1H-indole-1-acetic acid, ethyl ester was also isolated as a by product from the reaction (0.33 g).

$^1$H NMR (DMSO) δ 7.32 (dd, 2H), 7.01 (dd, 2H), 6.95 (t, 1H), 6.73 (d, 1H), 6.16 (d, 1H), 5.70 (t, 1H), 5.11 (s, 2H), 4.16 (q, 2H), 3.05 (dt, 2H), 2.34 (s, 31), 1.21 (t, 3H), 1.02 (t, 3H).

b) 4-(acetylamino)-3-[(4-chlorophenyl)thio]-2-methyl-1H-indole-acetic acid, ethyl ester To a solution of the product from part (a) (0.5 g) in dichloromethane (10 ml) was added triethylamine (0.18 ml) and acetyl chloride (0.1 ml), the reaction was stirred at room temperature for 30 minutes. The mixture was then adsorbed onto silica gel and purified by flash column chromatography (33% EtOAc/hexane as eluent) to give the subtitle compound (0.52 g).

$^1$H NMR (DMSO) δ 9.51 (s, 1H), 7.46 (d, 1H), 7.34-7.27 (m, 3H), 7.11(t, 1H), 6.97 (d, 2H), 5.24 (s, 2H), 4.18 (q, 2H), 2.39 (s, 3H), 1.86 (s, 3H), 1.21 (t, 3H).

c) 4-(acetylamino)-3-[(4-chlorophenyl)sulfonyl]-2-methyl-1H-indole-1-acetic acid, ethyl ester The subtitle compound was prepared by the method of example 20 part (c) using the product from part (b). Used without further characterisation in part (d).

d) 4-(acetylamino)-3-[(4-chlorophenyl)sulfonyl]-2-methyl-1H-indole-1-acetic acid The title compound was prepared by the method of example 2 part (d) using the product from part (c). Product was purified using reverse phase preparative HPLC (eluent MeCN/NH$_3$(aq)).

$^1$H NMR (DMSO) δ 10.34 (1H, s), 8.01 (1H, d), 7.77 (2H, dt), 7.67 (2H, m), 7.29 (1H, d), 7.19 (1H, t), 4.82 (2H, s), 2.66 (3H, s), 2.06 (3H, s). APCI− (M−H) 419

EXAMPLE 22

3-[(4-chlorophenyl)sulfonyl]-2-methyl-4-[(methylsulfonyl)amino]-1H-indole-1-acetic acid

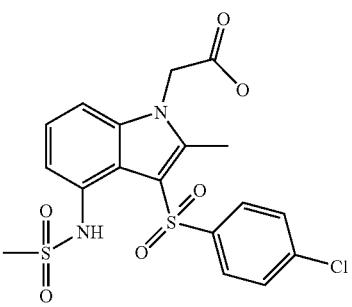

a) 4-amino-3-[(4-chlorophenyl)sulfonyl]-2-methyl-1H-indole-1-acetic acid, ethyl ester A suspension of the product from example 20 part (c) (1 g) in glacial acetic acid (50 ml) was stirred in the presence of 5% Pt/C (0.5 g) under 3 bar pressure of $H_2$ for 24 hours. The catalyst was removed by filtration and the filtrates concentrated in vacuo. Purification by flash column chromatography (20% EtOAc/hexane as eluent) gave the subtitle compound (0.45 g).

$^1$H NMR (DMSO) δ 7.89 (2H, dt), 7.66 (2H, dt), 6.96 (1H, t), 6.72 (1H, d), 6.45 (1H, d), 5.96 (2H, s), 5.13 (2H, s), 4.14 (2H, q), 2.63 (3H, s), 1.18 (3H, t)

3-[(4-chlorophenyl)sulfonyl]-4-(ethylamino)-2-methyl-1H-indole-1-acetic acid, ethyl ester was isolated as a by product from the reaction.

$^1$H NMR (DMSO) δ 7.83 (2H, dd), 7.67 (2H, dt), 7.06 (1H, t), 6.78 (1H, d), 6.72 (1H, t), 6.31 (1H, d), 5.16 (2H, s), 4.15 (2H, q), 3.12 (2H, dt), 2.65 (3H, s), 1.28-1.16 (6H, m)

b) 3-[(4-chlorophenyl)sulfonyl]-2-methyl-4-[(methylsulfonyl)amino-1H-indole-1-acetic acid, ethyl ester To a solution of the product from part (a) (0.2 g) in acetonitrile (10 ml) was added triethylamine (72 ul) and methane sulfonylchloride (41 ul), the reaction was heated to reflux overnight. The mixture was then adsorbed onto silica gel and purified by flash column chromatography (33% EtOAc/hexane as eluent) to give the subtitle compound (0.18 g)

$^1$H NMR (DMSO) δ 9.83 (1H, s), 7.84 (2H, d), 7.71 (2H, d), 7.40 (1H, d), 7.33-7.27 (2H, m), 5.31 (2H, s), 4.17 (2H, q), 2.99 (3H, s), 2.68 (3H, s), 1.20 (3H, t)

c) 3-[(4-chlorophenyl)sulfonyl]-2-methyl-4-[(methylsulfonyl)amino]-1H-indole-1-acetic acid The title compound was prepared by the method of example 2 part (d) using the product of part (b). The product was recystallised from boiling aqueous ethanol.

$^1$H NMR (DMSO) δ 9.84 (1H, s), 7.84 (2H, dt), 7.71 (2H, dt), 7.40 (1H, dd), 7.33-7.27 (2H, m), 5.15 (2H, s), 2.98 (3H, s), 2.68 (3H, s)

MS: APCI– [M–H] 455
m.p. dec >237° C.

EXAMPLE 23

3-[(4-chlorophenyl)sulfonyl]-4-(ethylamino)-2-methyl-1H-indole-1-acetic acid

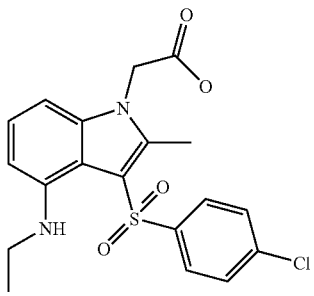

a) 3-[(4-chlorophenyl)sulfonyl]-4-(ethylamino)-2-methyl-1H-indole-1-acetic acid

The title compound was prepared by the method of example 2 part (d) using the by product from example 22 part (a). Product was purified using reverse phase preparative HPLC.

$^1$H NMR (DMSO) δ 7.83 (2H, dt), 7.65 (2H, dt), 7.02 (1H, t), 6.73-6.69 (2H, m), 6.27 (1H, d), 4.68 (2H, s), 3.12 (2H, dt), 2.62 (3H, s), 1.25 (3H, t)

MS: APCI– [M–H] 405

EXAMPLE 24

3-[(2,6-Dichlorophenyl)sulfonyl]-2,5-dimethyl-1H-indole-1-acetic acid

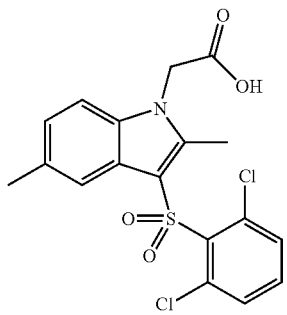

a) 3-[(2,6-Dichlorophenyl)thio]-2,5-dimethyl-1H-indole-1-acetic acid

Iodine (0.51 g) was added to a solution of 2,6-dichlorobenzenethiol (0.36 g) and the product from example 13 step a) (0.2 g) in DMF (5 ml). After 1 h the solution was purified by reverse phase HPLC. The solvent was evaporated in vacuo and the oily residue treated with ether to give a solid. Filtered off and dried to yield the title compound as a white solid (0.22 g).

MS: APCI– [M–H]⁻ 378
$^1$H NMR δ$_{(DMSO)}$ 7.49 (2H, d), 7.29 (1H, m), 7.24 (1H, d), 7.13 (1H, s), 6.88 (1H, d), 4.81 (2H, s), 2.44 (3H, s), 2.29 (3H, s)

b) 3-[(2,6-Dichlorophenyl)sulfonyl]-2,5-dimethyl-1H-indole-1-acetic acid

3-Chlorobenzenecarboperoxoic acid (0.34 g) was added to a solution of the product from example 24 step a) (0.18 g) in acetonitrile (5 ml) and water (0.5 ml). The reaction was stirred for 1 h, 1M aqueous sodium thiosulphate (2 ml) added and stirred for a further 15 min. The mixture was filtered, purified by reverse phase HPLC and evaporated in vacuo to yield the title compound as a white solid (40 mg).

MS: APCI– 410 [M–H]⁻
$^1$H NMR δ$_{(DMSO)}$ 7.64-7.60 (2H, m), 7.57-7.51 (1H, m), 7.45 (1H, s), 7.42 (1H, d), 7.03 (1H, d), 5.01 (2H, s), 2.60 (3H, s), 2.33 (3H, s)

EXAMPLE 25

3-[(4-chlorophenyl)sulfonyl]-2-methyl-4-phenyl-1H-indol-1-acetic acid

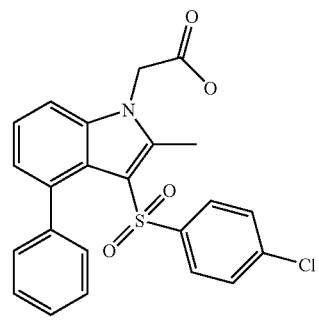

a) 4-bromo-3-[4(-chlorophenyl)thio]-2-methyl-1H-indole

The subtitle compound was prepared by the method of example 2 part (a) using (3-bromophenyl)-hydrazine hydrochloride. Product purified using Flash column chromatography (10% EtOAc/hexane as eluent).

$^1$H NMR(CDCl$_3$) δ 7.31 (1H, s), 7.30 (2H, d), 7.13 (2H, dt), 7.02 (1H, t), 6.94 (2H, dt), 2.52 (3H, s).

b) 4-bromo-3-[(4-chlorophenyl)thio]-2-methyl-1H-indole-1-acetic acid, 1,1-dimethylethyl ester The subtitle compound was prepared by the method of example 20 part (b) using the product of part (a) and t-butyl-bromoacetate. Product was purified using Flash column chromatography
(110% EtOAc/hexane as eluent).

$^1$H NMR(CDCl$_3$) d 7.31 (1H, dd), 7.21 (1H, dd), 7.14-7.10 (2H, m), 7.05 (1H, t), 6.94-6.91 (2H, m), 4.77 (2H, s), 2.49 (3H, s), 1.43 (9H, s).

c) 3-[(4-chlorophenyl)thio]-2-methyl-4-phenyl-1H-indole-1-acetic acid, 1,1-dimethylethyl ester To a solution of the product of part (b) (0.5 g) in ethanol (0.8 ml) and toluene (3 ml) was added 2 M sodium carbonate solution in water (1.4 ml), phenylboronic acid (0.131 g) and tetrakis(triphenylphosphine)palladium(0) (1.2 g). The reaction was heated to reflux for 2 hours, cooled and concentrated in vacuo. The residue was purified by flash column chromatography to give the subtitle compound (0.4 g).
$^1$H NMR (DMSO) d 7.53 (1H, d), 7.25-7.18 (2H, m), 7.15-7.09 (6H, m), 6.87 (1H, d), 6.54 (2H, m), 5.17 (2H, s), 2.39 (3H, s), 1.43 (9H, s).

d) 3-[(4-chlorophenyl)sulfonyl]-2-methyl-4-phenyl-1H-indole-1-acetic acid 1,1-dimethylethyl ester The subtitle compound was prepared by the method fo example 20 part (c) using the product from part (c). The product was used without further characterisation in part (e).

e) 3-[(4-chlorophenyl)sulfonyl]-2-methyl-4-phenyl-1H-indole-1-acetic acid

The title compound was prepared by the method of example 2 part (d) with the addition that the reaction mixture was heated to reflux for 20 minutes. Product was purified using reverse phase preparative HPLC (eluent MeCN/NH$_3$ (aq)).
$^1$H NMR (DMSO) δ 7.51-7.41 (3H, m), 7.24-7.12 (4H, m), 7.06 (2H, t), 6.82 (2H, d,), 6.75 (1H, d), 4.68 (2H, s), 2.73 (3H, s)
MS: APCI− [M−H] 438

EXAMPLE 26

3-[(4-chlorophenyl)sulfonyl]-5-fluoro-2-methyl-1H-indole-1-acetic acid, ammonium salt

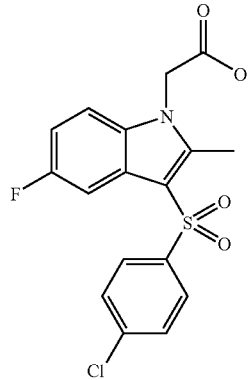

a) 5-fluoro-2-methyl-1H-indole-1-acetic acid methyl ester

A mixture of 5-fluoro-2-methylindole (2.4 g), cesium carbonate (16.6 g) and methyl bromoacetate (5.4 ml) in acetone 240 ml was stirred and heated under reflux for 16 h. The solvent was removed, water and ethyl acetate were added and the organic phase separated. The aqueous phase was re-extraced with ethyl acetate and the combined organic solution dried and concentrated to a solid. Purification by flash chromaography using dichloromethane:ethylacetate gave the subtitle compound as a solid (2.9 g)
MS: APCI+ [M+H] 222 b) 5-fluoro-2-methyl-1H-indole-1-acetic acid

The product from step a) was dissolved in THF (30 ml) and a solution of LiOH.H20 (0.91 g) in H$_2$O (10 m]) was added. After 24 h the solvent was removed, 10% (aq) HCl and ethyl acetate were added and the organic phase separated. The aqueous phase was re-extraced with ethyl acetate and the combined organic solution washed with brine, dried and concentrated to an oil. Purification by flash chromaography using dichloromethane:ethylacetate gave the subtitle compound as a yellow powder (1.2 g).
MS: APCI [M−H]$^-$ 206 c) 3-[(4-chlorophenyl)thio]-5-fluoro-2-methyl-1H-indole-1-acetic acid

Iodine (0.98 g) was added to a solution of 4-chlorolbenzenethiol (0.55 g) and the product from step b) (0.4 g) in NMP (5 ml). The solution was stirred for 24 h and the crude product purified by reverse phase chromatography to give the subtitle compound as a solid (0.29 g)
MS: APCI [M−H]$^-$ 348/50
$^1$H NMR (DMSO) δ 7.4 (1H, m), 7.25 (2H, d), 7.0-6.9 (4H, m), 4.59 (2H, s), 2.37 (3H, s).

d) 3-[(4-chlorophenyl)sulfonyl]-5-fluoro-2-methyl-1H-indole-1-acetic acid, ammonium salt 3-Chlorobenzenecarboperoxoic acid (0.4 g) was added to a solution of the product from step c) (0.19 g) in acetonitrile (4 ml). The reaction was stirred for 3 h, 1M aqueous sodium thiosulphate (5 ml) was added and stirred for a further 15 min, 10% aqueous HCl and ethyl acetate were added and the organic phase separated. The aqueous phase was re-extracted with ethyl acetate and the combined organic solution washed with brine, dried and concentrated to a solid which was purified by reverse phase chromatography to give the title compound as a solid (0.12 g)
MS: APCI [M−H]$^-$ 380/82
$^1$H NMR (DMSO) δ 7.94 (2H, m), 7.62(2H, m), 7.6-7.55 (2H, m), 7.4-6.8 (1H bs), 7.05 (1H, dt), 4.8 (2H, s), 2.61 (3H, s).

EXAMPLE 27

3-[(3-chlorophenyl)sulfonyl]-5-fluoro-2-methyl-1H-indole-1-acetic acid, ammonium salt

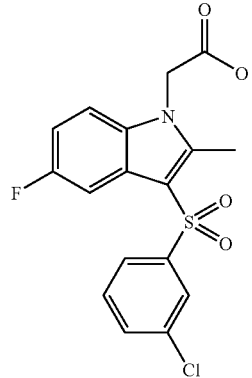

a) 3-[(3-chlorophenyl)thio]-5-fluoro-2-methyl-1H-indole-1-acetic acid

Prepared by the method of example 26 step c) using the product of example 26 step b) (0.55 g), iodine (0.98 g) and 3-chlorolbenzenethiol to give the subtitle compound as a solid (0.25 g)

MS: APCI [M–H]⁻ 348/50

¹H NMR (DMSO) δ 7.4 (1H, m), 7.2 (1H, m), 7.16 (1H, m), 7.0-6.95 (4H, m), 4.57 (2H, s), 2.28 (3H, s)

b) 3-[(3-chlorophenyl)sulfonyl]-5-fluoro-2-methyl-1H-indole-1-acetic acid, ammonium salt Prepared by the of example 26 step d) using the product of example 27 step a) (0.15 g) and 3-chlorobenzenecarboperoxoic acid (0.32 g) to give the title compound as a solid (0.09 g).

MS: APCI [M–H]⁻ 380/82

¹H NMR (DMSO) δ 7.94 (2H, m), 7.7 (1H, m), 7.6 (2H, m), 7.55 (1H, m), 7.2-7.0 (1H bs), 7.05 (1H, dt), 4.79 (2H, s), 2.63 (3H, s).

EXAMPLE 28

5-fluoro-2-methyl-3-[[4-(trifluoromethyl)phenyl]sulfonyl]-1H-indole-1-acetic acids ammonium salt

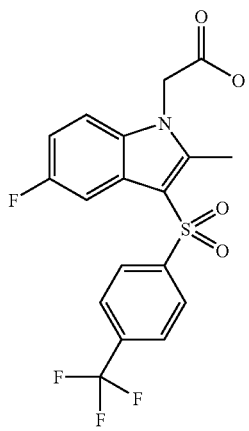

a) 5-fluoro-2-methyl-3-[[4-(trifluoromethyl)phenyl]thio]-1H-indole-1-acetic acid Prepared by the method of example 26 step c) using the product of example 26 step b) (0.55 g), iodine (0.98 g) and 4-trifluoromethylbenzenethiol (0.67 g) to give the subtitle compound as a solid (0.25 g).

MS: APCI [M–H]⁻ 382

¹H NMR (DMSO) δ 7.57 (3H, m), 7.05 (2H, m), 7.02 (2H, m), 5.0 (2H, s), 2.4 (3H, s)

b) 5-fluoro-2-methyl-3-[[4-(trifluoromethyl)phenyl]sulfonyl]-1H-indole-1-acetic acid, ammonium salt Prepared by the method of example 26 step d) using the product of example 28 step a) (0.17 g) and 3-chlorobenzenecarboperoxoic acid (0.33 g) to give the title compound as a solid (0.11 g).

MS: APCI [M–H]⁻ 414

¹H NMR (DMSO) δ 8.18 (211, d), 7.95 (2H, d), 7.65-58 (2H, m), 7.2-6.9 (1H, bs), 7.14-7.09 (1H, m), 5.02 (2H, s), 2.67 (3H, s).

Pharmacological Data

Ligand Binding Assay

[³H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Fetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 μl of 6.25 nM [³H]PGD$_2$, 20 μl membrane saturated SPA beads both in assay buffer and 10 μl of compound solution or 13,14-dihydro-15-keto prostaglandin D$_2$ (DK-PGD$_2$, for determination of non-specific binding Cayman chemical company). Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10 μM. Specifically example 2 has a pIC$_{50}$=8.1 example 6 has a pIC$_{50}$=7 and example 7 has a pIC$_{50}$=6.6

The invention claimed is:

1. A compound of formula (I) or a pharmaceutically acceptable salt thereof:

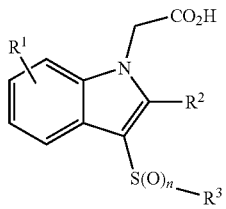

in which:

n represents 1 or 2;

$R^1$ is one or more substituents independently selected from halogen, CN, nitro, $SO_2R^4$, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, aryl, $C_2$-$C_6$ alkenyl, $C_2$-$C_6$ alkynyl or $C_{1-6}$alkyl, the latter five groups being optionally substituted by one or more substituents independently selected from halogen, $OR^7$ and $NR^8R^9$, $NR^8R^9$, $S(O)_xR^7$ where x is 0, 1 or 2;

$R^2$ is hydrogen, halogen, CN, $SO_2R^4$ or $CONR^5R^6$, $COR^4$ or $C_{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is aryl or a 5-6 membered aromatic ring containing one or more heteroatoms selected from N, S and O, each of which is optionally substituted by one or more substituents independently selected from halogen, CN, nitro, $SO_2R^4$, OH, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, $C_2$-$C_6$ alkenyl, $C_2$-$C_6$ alkynyl, $C_1$-$C_6$ alkyl, the latter three groups being optionally substituted by one or more substituents independently selected from halogen atoms, $OR^7$ and $NR^8R^9$, $S(O)_xR^7$ where x is 0, 1 or 2;

$R^4$ represents aryl, heteroaryl, or $C_1$-$C_6$ alkyl, all of which are optionally substituted by one or more substituents independently selected from halogen atoms, aryl, heteroaryl, $OR^{10}$ and $NR^{11}R^{12}$ $S(O)_xR^{13}$ (where x=0, 1 or 2), $CONR^{14}R^{15}$, $NR^{14}COR^{15}$, $SO_2NR^{14}R^{15}$, $NR^{14}SO_2R^{15}$, CN, nitro;

$R^5$ and $R^6$ independently represent a hydrogen atom, a $C_1$-$C_6$ alkyl group, or an aryl group, the latter two of which may be optionally substituted by one or more substituents independently selected from halogen atoms, aryl, $OR^{13}$ and $NR^{14}R^{15}$, $CONR^{14}R^{15}$, $NR^{14}COR^{15}$, $SO_2NR^{14}R^{15}$, $NR^{14}SO_2R^{15}$, CN, nitro;

or $R^5$ and $R^6$ together with the nitrogen atom to which they are attached can form a 3-8 membered saturated heterocylic ring optionally containing one or more atoms selected from O, $S(O)_x$ where x is 0, 1 or 2, $NR^{16}$, and the ring itself is optionally substituted by $C_1$-$C_3$ alkyl;

$R^7$ and $R^{13}$ independently represent a $C_1$-$C_6$ alkyl group, or an aryl or group all of which are optionally substituted by halogen atoms;

$R^8$ represents a hydrogen atom, $C(O)R^9$, $C_1$-$C_6$ alkyl (optionally substituted by halogen atoms, or an aryl group, which also is optionally substituted by one or more fluorine atoms); or an aryl group, which is optionally substituted by one or more halogen atoms;

each of $R^9$, $R^{10}$, $R^{11}$, $R^{12}$, $R^{14}$, $R^{15}$, independently represents a hydrogen atom, $C_1$-$C_6$ alkyl, or an aryl group (all of which may be optionally substituted by one or more halogen atoms); and $R^{16}$ is hydrogen, $C_{1-4}$ alkyl, —$C(O)C_1$-$C_4$ alkyl, $C(O)YC_1$-$C_4$alkyl, Y is O or $NR^7$.

2. A compound according to claim 1 in which n is 2.

3. A compound according to claim 1 in which $R^1$ is halogen, nitrile, $C_{1-6}$alkyl or $SO_2R^4$, $NO_2$, $NR^9COR^4$, $NR^9SO_2R^4$, aryl, $NR^5R^6$.

4. A compound according to claim 1 in which the $R^1$ substituent(s) is/are in the 4- and/or 5-position.

5. A compound according claim 1 in which $R^2$ is $C_{1-6}$alkyl.

6. A compound according to claim 4 in which $R^3$ is phenyl substituted by halogen.

7. A compound according to claim 1 selected from:

3 -[(4-chlorophenyl)sulfonyl]-2,5-dimethyl-1H-indol-1-acetic acid;

5-chloro-3-[(4-chlorophenyl)sulfonyl]-2-methyl-1H-indole-1-acetic acid;

6-chloro-3-[(4-chlorophenyl)sulfonyl]-2-methyl-1H-indole-1-acetic acid;

7-chloro-3-[(4-chlorophenyl)sulfonyl]-2-methyl-1H-indole-1-acetic acid;

5-chloro-3-[(4-chlorophenyl)sulfonyl]-4-cyano-2-methyl-1H-indole-1-acetic acid;

5-chloro-3-[(4-chlorophenyl)sulfonyl]-6-cyano-2-methyl-1H-indole-1-acetic acid;

3-[(4-chlorophenyl)sulfonyl]-2,5-dimethyl-1H-indole-1-acetic acid;

3-[(4-chlorophenyl)sulfonyl]-4-(ethylsulfonyl)-7-methoxy-2-methyl-1H-indole-1-acetic acid;

3-[(4-chlorophenyl)sulfonyl]-5-cyano-2-methyl-1H-indole-1-acetic acid;

3-[(4-chlorophenyl)sulfonyl]-5-cyano-2-methyl-1H-indole-1-acetic acid;

5-chloro-3-[(4-chlorophenyl)sulfonyl]-2-methyl-1H-indole-1-acetic acid, 4-chloro-3-[(4-chlorophenyl)sulfonyl]-2-methyl-1H-indole-1-acetic acid;

3-[(4-methoxyphenyl)sulfonyl]-2,5-dimethyl-1H-indol-1-acetic acid;

3-[(3-methoxyphenyl)sulfonyl]-2,5-dimethyl-1H-indol-1-acetic acid;

3-[(2-Chlorophenyl)sulfonyl]-2,5-dimethyl-1H-indol-1-acetic acid;

3-[(3-Chlorophenyl)sulfonyl]-2,5-dimethyl-1H-indol-1-acetic acid;

3-[(4-Cyanophenyl)sulfonyl]-2,5-dimethyl-1H-indole-1-acetic acid;

3-[(2-methylphenyl)sulfonyl]-2,5-Dimethyl-1H-indol-1-acetic acid;

3-[(2-ethylphenyl)sulfonyl]-2,5-dimethyl-1H-indol-1-acetic acid;

3-[(4-chlorophenyl)sulfonyl]-2-methyl-4-nitro-1H-indole-1-acetic acid;

4-(Acetylamino)-3-[(4-chlorophenyl)sulfonyl]-2-methyl-1H-indole-1-acetic acid;

3-[(4-chlorophenyl)sulfonyl]-2-methyl-4-[(methylsulfonyl)amino]-1H-indole-1-acetic acid;

3-[(4-chlorophenyl)sulfonyl]-4-(ethylamino)-2-methyl-1H-indole-1-acetic acid;

3-[(2,6-Dichlorophenyl)sulfonyl]-2,5-dimethyl-1H-indole-1-acetic acid;

3-[(4-chlorophenyl)sulfonyl]-2-methyl-4-phenyl-1H-indole-1-acetic acid

3-[(4-chlorophenyl)sulfonyl]-5-fluoro-2-methyl-1H-indole-1-acetic acid,

3-[(3 -chlorophenyl)sulfonyl]-5-fluoro-2-methyl-1H-indole-1-acetic acid, and 5-fluoro-2-methyl-3-[[4-(trifluoromethyl)phenyl]sulfonyl]-1H-indole-1-acetic acid, or a pharmaceutically acceptable salt thereof.

8. A method of treating asthma or rhinitis, the method comprising administering to a patient a therapeutically effective amount of a compound of formula (I), or a pharmaceutically acceptable salt as defined in claim 1.

9. A process for the preparation of a compound of formula (I) of claim 1 which comprises:
(a) oxidation of a compound of formula (II):

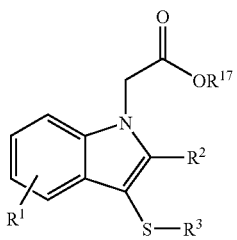

(II)

in which $R^{17}$ is hydrogen or alkyl and $R^1$, $R^2$ and $R^3$ are as defined in claim 1, or (b) reaction of a compound of formula (III):

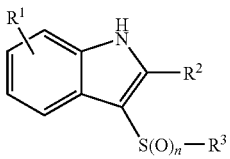

(III)

in which $R^1$, $R^2$ and $R^3$ are as defined in claim 1, with a compound of formula (IV):

$R^{18}$—O(CO)CH$_2$-L (IV)

where $R^{18}$ is an alkyl group and L is a leaving group in the presence of a base, and optionally thereafter (a) or (b) in any order:

hydrolysing the ester group $R^{17}$ $R^{18}$ to the corresponding acid removing any protecting group forming a pharmaceutically acceptable salt.

10. A compound of formula (II):

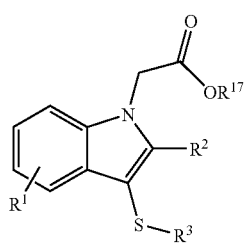

(II)

wherein:

$R^{17}$ is hydrogen or alkyl;

$R^1$ is one or more substituents independently selected from $NR^9SO_2R^4$, $NR^9CO_2R^4$, and $NR^9COR^4$;

$R^2$ is hydrogen, halogen, CN, $SO_2R^4$ or $CONR^5R^6$, $COR^4$ or $C^{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is aryl or a 5-6 membered aromatic ring containing one or more heteroatoms selected from N, S and O, each of which is optionally substituted by one or more substituents independently selected from halogen, CN, nitro, $SO_2R^4$, OH, $OR^4$, $SR^4$, $SOR^4$, $SO_2NR^5R^6$, $CONR^5R^6$, $NR^5R^6$, $NR^9SO_2R_4$, $NR^9CO_2R^4$, $NR^9COR^4$, $C_2$-$C_6$ alkenyl, $C_2$-$C_6$ alkynyl, $C_1$-$C_6$ alkyl, the latter three groups being optionally substituted by one or more substituents independently selected from halogen atoms, $OR^7$ and $NR^8R^9$, $S(O)_xR^7$ where x is 0, 1 or 2;

$R^4$ represents aryl, heteroaryl, or $C_1$-$C_6$ alkyl, all of which are optionally substituted by one or more substituents independently selected from halogen atoms, aryl, heteroaryl, $OR^{10}$ and $NR^{11}R^{12}S(O)_xR^{13}$ (where x=0, 1 or 2), $CONR^{14}R^{15}$, $NR^{14}COR^{15}$, $SO_2NR^{14}R^{15}$, $NR^{14}SO_2R^{15}$, CN, nitro;

$R^5$ and $R^6$ independently represent a hydrogen atom, a $C_1$-$C_6$ alkyl group, or an aryl group, the latter two of which are optionally substituted by one or more substituents independently selected from halogen atoms, aryl, $OR^{13}$ and $NR^{14}R^{15}$, $CONR^{14}R^{15}$, $NR^{14}COR^{15}$, $SO_2NR^{14}R^{15}$, $NR^{14}SO_2R^{15}$, CN, nitro;

or $R^5$ and $R^6$ together with the nitrogen atom to which they are attached can form a 3-8 membered saturated heterocylic ring optionally containing one or more atoms selected from O, $S(O)_x$ where x is 0, 1 or 2, $NR^{16}$, and the ring itself optionally substituted by $C_1$-$C_3$ alkyl;

$R^7$ and $R^{13}$ independently represent a $C_1$-$C_6$ alkyl group, or an aryl or group all of which are optionally substituted by halogen atoms;

$R^8$ represents a hydrogen atom, C(O)$R^9$, $C_1$-$C_6$ alkyl (optionally substituted by halogen atoms, or an aryl group, which is optionally substituted by one or more fluorine atoms); an aryl group, which is optionally substituted by one or more halogen atoms;

each of $R^9$, $R^{10}$, $R^{11}$, $R^{12}$, $R^{14}$, $R^{15}$, independently represents a hydrogen atom, $C_1$-$C_6$ alkyl, or an aryl group (all of which are optionally substituted by one or more halogen atoms); and $R^{16}$ is hydrogen, $C_{1-4}$ alkyl, —C(O)$C_1$-$C_4$ alkyl, C(O)Y$C_1$-$C_4$alkyl, Y is O or $NR^7$.

11. A compound according to claim 10 in which the $R^1$ substituent(s) is/are in the 4- and/or 5-position.

12. A compound according claim 10 in which $R^2$ is $C_{1-6}$alkyl.

13. A compound according to claim 10 in which $R^3$ is phenyl substituted by halogen.

14. A compound according to claim 10 in which $R^1$ is one or more substituents independently selected from $NR^9SO_2R^4$ and $NR^9COR^4$.

15. A compound according to claim 14 in which the $R^1$ substituent(s) is/are in the 4- and/or 5-position.

16. A compound according to claim 14 in which $R^2$ is $C_{1-6}$alkyl.

17. A compound according to claim 14 in which $R^3$ is phenyl substituted by halogen.

* * * * *

UNITED STATES PATENT AND TRADEMARK OFFICE
CERTIFICATE OF CORRECTION

PATENT NO. : 7,723,373 B2  
APPLICATION NO. : 10/521325  
DATED : May 25, 2010  
INVENTOR(S) : Roger Bonnert et al.

Page 1 of 1

It is certified that error appears in the above-identified patent and that said Letters Patent is hereby corrected as shown below:

Column 37, line 49 (Approx.), "group,or", should read -- group, or --.

Column 37, line 50 (Approx.), "may be", should read -- are --.

Column 38, line 3, "may be", should read -- are --.

Column 38, line 13, "according", should read -- according to --.

Column 38, line 17, "3 -[(4", should read -- 3-[(4 --.

Column 38, line 67, "acid", should read -- acid; --.

Column 39, line 3, "3 -chlorophenyl", should read -- 3-chlorophenyl --.

Column 39, line 44 (Approx.), "$R^{17} R^{18}$", should read -- $R^{17}$ or $R^{18}$ --.

Column 40, line 41 (Approx.), "atoms);", should read -- atoms); or --.

Column 40, line 51, "according", should read -- according to --.

Signed and Sealed this  
Twenty-second Day of February, 2011

David J. Kappos  
*Director of the United States Patent and Trademark Office*